US012522864B2

(12) United States Patent
Santamarina

(10) Patent No.: US 12,522,864 B2
(45) Date of Patent: Jan. 13, 2026

(54) PROCESS FOR THE PRODUCTION OF CLOSED LINEAR DNA

(71) Applicant: TYRIS THERAPEUTICS, S.L., Moncada (ES)

(72) Inventor: Julen Oyarzabal Santamarina, Madrid (ES)

(73) Assignee: TYRIS THERAPEUTICS, S.L., Moncada (ES)

( * ) Notice: Subject to any disclaimer, the term of this patent is extended or adjusted under 35 U.S.C. 154(b) by 756 days.

(21) Appl. No.: 17/796,596

(22) PCT Filed: Jan. 29, 2021

(86) PCT No.: PCT/EP2021/052203
§ 371 (c)(1),
(2) Date: Jul. 29, 2022

(87) PCT Pub. No.: WO2021/152146
PCT Pub. Date: Aug. 5, 2021

(65) Prior Publication Data

US 2023/0075380 A1 Mar. 9, 2023

(30) Foreign Application Priority Data

Jan. 31, 2020 (EP) .................................... 20382064

(51) Int. Cl.
*C12Q 1/6844* (2018.01)
*C12N 15/10* (2006.01)

(52) U.S. Cl.
CPC .................................. *C12Q 1/6844* (2013.01)

(58) Field of Classification Search
None
See application file for complete search history.

(56) References Cited

U.S. PATENT DOCUMENTS

| | | | |
|---|---|---|---|
| 6,451,563 B1 | 9/2002 | Wittig et al. | |
| 8,404,808 B2 | 3/2013 | Falgueras et al. | |
| 9,109,250 B2 * | 8/2015 | Hill ...................... | C12Q 1/6853 |
| 11,299,718 B2 * | 4/2022 | Picher .................... | C12Q 1/686 |
| 2013/0216562 A1 | 8/2013 | Porter et al. | |
| 2019/0185924 A1 | 6/2019 | Adie et al. | |
| 2020/0362403 A1 * | 11/2020 | Serantes .............. | C12Q 1/6855 |

FOREIGN PATENT DOCUMENTS

| | | |
|---|---|---|
| WO | WO 2011/000997 A1 | 1/2011 |
| WO | WO 2019/101596 A1 | 5/2019 |
| WO | WO 2019/118806 A1 | 6/2019 |

OTHER PUBLICATIONS

Xiao et al (1997, Journal of Virology, 71:941-948.*
International Search Report and Written Opinion mailed May 11, 2021 for PCT Application No. PCT/EP2021/052203; 17 pages.
Altschul, et al: "Basic local alignment search tool", J. Mol. Biol 1990; vol. 215, pp. 403-410.
Beaucage, et al: "Deoxynucleoside phosphoramidites—A new class of key intermediates for deoxypolynucleotide synthesis", Tetrahedron Letters 1981, vol. 22, Issue 20, pp. 1859-1862.
Calus, et al: "NanoAmpli-Seq: A workflow PC for amplicon sequencing for mixed microbial communities on the nanopore sequencing platform.", bioRxiv, Jul. 4, 2018 (Jul. 4, 2018), DOI: 10.1101/244517.
Picher, et al: "TruePrime is a novel method for whole-genome amplification from single cells based on TthPrimPol", Nature Communications, vol. 7, No. 1, Dec. 1, 2016 (Dec. 1, 2016), XP055797801, DOI: 10.1038/ncornms13296.
Heinrich, et al: "Linear closed mini DNA generated by the prokaryotic cleaving-joining enzyme TelN is functional in mammalian cells" J Mol Med; Aug. 28, 2002; vol. 80(10), pp. 648-654.
Xiao, et al., "A novel 165-base-pair terminal repeat sequence is the sole cis requirement for the adeno-associated virus life cycle", Journal of Virology; Feb. 1997; vol. 71(2), pp. 941-948.

* cited by examiner

*Primary Examiner* — Jason Deveau Rosen
(74) *Attorney, Agent, or Firm* — Squire Patton Boggs (US) LLP

(57) ABSTRACT

The present invention provides a process for the production of a closed linear DNA comprising the steps of (a) providing a DNA template comprising a DNA sequence of interest; (b) amplifying DNA from the DNA template of step (a) wherein the amplification is primed with a primase/polymerase enzyme; (c) generating a closed linear DNA with the amplified DNA produced in step (b); and (d) purifying the closed linear DNA produced in step (c). The invention also provides a closed linear DNA obtainable according to the process of the invention, a pharmaceutical composition comprising a therapeutically effective amount of the closed linear DNA of the invention, and a concatameric DNA comprising repeats of a DNA sequence of interest.

15 Claims, 9 Drawing Sheets

Specification includes a Sequence Listing.

| Sample | Produced reads | Mapped reads | Percentage |
|---|---|---|---|
| PrimPol | 10,628,762 | 8,419,939 *100%* | 79.22% |
| RPs | 12,467,258 | 8,198,854 *97,4%* | 65,76% |

A

B

| Sample name | Expected band percentage (%) | Unspecific band 1 percentage (%) |
|---|---|---|
| oDNA-41 | 96.2 | 3.8 |

D

| Sample name | Expected band percentage (%) | Unspecific band 2 percentage (%) |
|---|---|---|
| oDNA-21 | 95.6 | 4.4 |

pDNA_eGFP pDNA_Luc_ITR2

PROCESS FOR THE PRODUCTION OF CLOSED LINEAR DNA

CROSS-REFERENCE TO RELATED APPLICATIONS

The present application is a 35 U.S.C. § 371 national-phase filing of International Application No. PCT/EP2021/052203, filed on Jan. 29, 2021, which claims the benefit of European Patent Application EP20382064.2 filed on Jan. 31, 2020, both of which are incorporated herein by reference in their entirety.

Incorporation By Reference

This application contains a sequence listing entitled "P5393PC00_ST25.txt," being submitted herein in ASCII format via EFS-Web, which is a copy of the sequence listing as filed in PCT/EP2021/052203, which was modified on Jun. 30, 2022 and is 36,485 bytes in size.

TECHNICAL FIELD

The present invention belongs to the field of nucleic acids and therapy. In particular, the invention relates to closed linear DNA as well as to a process for its preparation and pharmaceutical compositions comprising thereof. The closed linear DNA obtained by the process of the invention is particular useful for therapeutic purposes.

BACKGROUND ART

Gene therapy holds great promise for the treatment of several disease. It is based on the successful transfer of genetic material into the nuclei of targeted human cells. Gene delivery systems can be viral or non-viral in design. Compared with viral DNA vectors, non-viral transgene delivery systems offer safer gene transfer and vaccine design approaches, are less likely to elicit inflammatory and immune responses in hosts, have greater transgene capacity, and are easier to store.

However, the effectiveness of non-viral vectors is very limited, which has hindered their introduction to the clinic. For instance, the use of conventional plasmid DNA vectors for gene therapy can elicit adverse immune responses due to bacterial sequences they contain, and their bioavailability is compromised because of their large molecular size. Therefore, new types of non-viral DNA constructs have been developed in recent years.

Closed linear DNA vectors (clDNA) are dumbbell-shaped molecules solely comprising the DNA sequence of interest without the bulk of an immunogenic bacterial backbone, thus ensuring greater bioavailability, higher transfection efficiency, and prolonged duration of gene expression. The linear nature of the clDNA minimizes the potential for insertional mutagenesis from random genomic integration. clDNA vectors have been used successfully for various therapeutic indications with promising results in vitro and in vivo.

The production of nucleotide vectors, such as clDNA, for use in therapy presents various challenges. First, vectors should be free of any bacterial component or toxin that can produce adverse reactions on patients. Furthermore, the transfection efficiency of vectors into cells in vivo is rather low, therefore, very high production yields are required to reach the amounts needed for in vivo administration. Finally, injecting foreign nucleotide sequences into a patient is not without risks, for instance, the expression of mutated proteins or unspecific products generated during the production process can severely harm the patient.

In view of the above, vectors used in the clinic, in particular clDNAs, should be produced by processes that at the same time ensure the absence of bacterial remains and antibiotic resistance sequences, allow their large-scale production with reduced costs and also guarantee a very high degree of sequence homogeneity (i.e. a very low percentage of altered sequences).

Thus, in spite of the efforts made so far, there exists a need for efficient processes for the large-scale and safe production of clDNA with a quality suitable for therapeutic purposes.

SUMMARY OF INVENTION

The present inventors have developed a process for the large-scale production of clDNA with very high sequence quality which does not involve the use of microorganisms. The process herein provided is based on the use of a primase/polymerase for priming the amplification of a template DNA followed by the processing of the amplification products to generate clDNA suitable for therapy.

Surprisingly, as shown in the examples below, the inventors have found that by performing an amplification step primed by a primase/polymerase enzyme previous to clDNA formation not only a good production yield of clDNA was obtained, but also the sequence fidelity of the generated clDNA was highly improved compared to the use of other amplification processes, such as random priming (see FIG. 2). Thus, the results herein provided show that the priming is critical in the final properties of the clDNA obtained.

The high sequence quality provided by the primase/polymerase also impacts on the efficiency of the steps following amplification, which require the use of enzymes that recognize specific sequences on the amplified DNA. Thus, the high sequence fidelity provided by primase/polymerase priming ensures that all target sequences on the amplified DNA are highly conserved and can be efficiently targeted by the processing enzymes, such as restriction enzymes or protelomerases.

Remarkably, the absence of any step requiring the use of microorganisms makes the process of the invention also very easy to scale-up and safe.

Contrary to what is disclosed in the prior art, the inventors further found that the use of a primase/polymerase for priming the amplification of a clDNA template does not require the presence of primase recognition sites within the single stranded loops (i.e. the adaptors) of the template DNA. This greatly expands the repertoire of DNA templates that can be used in the process of the invention. For instance, a primase/polymerase can be used for priming clDNAs templates produced by the ligation of adaptors of any sequence (i.e. sequences not containing a primase/polymerase priming site), or clDNA templates generated by the action of a protelomerase, which contain minimal single stranded loops (see FIG. 4).

Finally, it was found that clDNA obtained by the process of the invention is suitable to be transfected into mammalian cells, and it also allows the efficient expression of a DNA sequence of interest contained therein (see FIGS. 5 and 6).

Altogether, in the examples provided below the inventors have demonstrated the utility of the process of the invention for the large-scale production of high quality clDNA suitable for gene therapy.

Thus, in a first aspect, the present invention provides a process for the production of a closed linear DNA comprising the steps of (a) providing a DNA template comprising a DNA sequence of interest; (b) amplifying DNA from the DNA template of step (a) wherein the amplification is primed with a primase/polymerase enzyme; (c) generating a closed linear DNA with the amplified DNA produced in step (b); and (d) purifying the closed linear DNA produced in step (c).

As mentioned above, the process of the invention allows the production of clDNA with a very high sequence fidelity (i.e. with a very low amount of amplification artifacts or mutated sequences), which makes them particularly suitable be used in therapy, where high sequence quality is an essential requirement.

Thus, in a second aspect, the invention provides a closed linear DNA obtainable according to the process as defined in the first aspect of the invention.

In a third aspect, the invention provides the closed linear DNA according to the second aspect for use in therapy.

In a fourth aspect, the invention provides a pharmaceutical composition comprising a therapeutically effective amount of the closed linear DNA according to the second aspect and pharmaceutically acceptable carriers or excipients.

In a fifth aspect, the invention provides a concatameric DNA comprising repeats of a DNA sequence of interest, wherein each one of the repeated DNA sequence of interest is flanked by at least recombinase recognition sites or, alternatively, by at least restriction sites and protelomerase target sequences.

DETAILED DESCRIPTION OF THE INVENTION

Figures 1, 2:
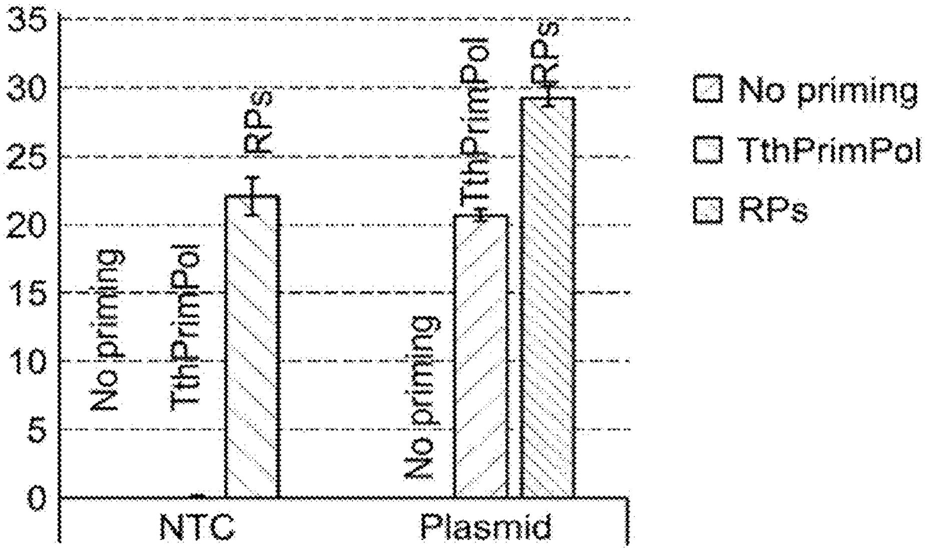
FIG. 1, related to Example 1, shows the DNA yield resulting from the RCA amplification of a DNA template where the amplification is primed either by TthPrimPol or random primers (RPs). The y-axis represents the DNA yield in µg. NTC refers to the control reaction, without template DNA; Plasmid refers to the amplification reaction with a plasmid template DNA.
FIG. 2, related to Example 1, shows the Illumina sequencing results comparing the amplification primed with TthPrimPol with the amplification primed with RPs.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

The invention provides in a first aspect a process for the production of a closed linear DNA comprising the steps of a) providing a DNA template comprising a DNA sequence of interest; b) amplifying DNA from the DNA template of step (a) wherein the amplification is primed with a primase/polymerase enzyme; c) generating a closed linear DNA with the amplified DNA produced in step (b); and d) purifying the closed linear DNA produced in step (c).

The amplification of the DNA template using a primase/polymerase as a priming enzyme, generates amplified DNA with very high efficiency and fidelity, which can be later processed to generate closed linear DNA suitable for therapeutic uses.

As used herein, the term "closed linear DNA" or "clDNA" refers to a single stranded covalently closed DNA molecule that forms a "dumbbell" or "doggy-bone" shaped structure under conditions allowing nucleotide hybridization. Therefore, although the clDNA is formed by a closed single stranded DNA molecule, the formation of the "dumbbell" structure by the hybridization of two complementary sequences within the same molecule generates a structure consisting on a double-stranded middle segment flanked by two single-stranded loops. The skilled in the art knows how to generate clDNA from open or closed double stranded DNA—such as the amplified DNA produced in step (b)—using routine molecular biology techniques. For instance, the skilled in the art knows that a clDNA can be generated by attaching single stranded hairpin adaptors—for instance, by the action of a ligase—to both ends of an open double stranded DNA. Another method known to the skilled in the art to generate closed linear DNA is through the action of a protelomerase on a double-stranded DNA that comprises at least two protelomerase target sequences.

The "sequence of interest" is understood as a double stranded DNA fragment that comprises the minimum necessary sequences encoding for the gene of interest together with other sequences that are required for correct gene expression, for example, an expression cassette. The sequence of interest may additionally comprise other sequences flanking the expression cassette, such as inverted terminal repeats (ITRs).

As used herein, the term "priming" refers to the generation of an oligonucleotide primer on a polynucleotide template by an enzyme.

The term "primase/polymerase enzyme" refers to a DNA-directed primase/polymerase enzyme, such as the enzymes from the archaeo-eukaryotic primase (AEP) superfamily. These enzymes present the capacity of starting DNA chains with dNTPs. Enzymes from this superfamily that can be used in the invention are, for example, *Thermus thermophilus* primase/polymerase (TthPrimPol) or human primase/polymerase (hsPrimPol, CCDC111, FLJ33167, EukPrim2 or hPrimPol1). "*Thermus thermophilus* primase/polymerase" or "TthPrimPol" refers to the primase/polymerase of the bacteria *Thermus thermophilus* of sequence SEQ ID NO: 1. The nucleotide and protein sequences are available in the NCBI Entrez database as NC_005835 and WP_01 1173100.1, respectively.

TABLE 1

| SEQ ID | Name | Sequence |
|---|---|---|
| SEQ ID NO: 1 | TthPrimPol | MRPIEHALSYAAQGYGVLPLRPGGKEPLGKLVPHGLKNASR<br>DPATLEAWWRSCPRCGVGILPGPEVLVLDFDDPEAWEGLR<br>QEHPALEAAPRQRTPKGGRHVFLRLPEGVRLSASVRAIPGV<br>DLRGMGRAYVVAAPTRLKDGRTYTWEAPLTPPEELPPVPQA<br>LLLKLLPPPPPPRPSWGAVGTASPKRLQALLQAYAAQVARTP<br>EGQRHLTLIRYAVAAGGLIPHGLDPREAEEVLVAAAMSAGLP<br>EWEARDAVRWGLGVGASRPLVLESSSKPPEPRTYRARVYA<br>RMRRWV |
| SEQ ID NO: 2 | TelN | MSKVKIGELINTLVNEVEAIDASDRPQGDKTKRIKAAAARYKN<br>ALFNDKRKFRGKGLQKRITANTFNAYMSRARKRFDDKLHHS<br>FDKNINKLSEKYPLYSEELSSWLSMPTANIRQHMSSLQSKLK<br>EIMPLAEELSNVRIGSKGSDAKIARLIKKYPDWSFALSDLNSD<br>DWKERRDYLYKLFQQGSALLEELHQLKVNHEVLYHLQLSPA<br>ERTSIQQRWADVLREKKRNVVVIDYPTYMQSIYDILNNPATLF<br>SLNTRSGMAPLAFALAAVSGRRMIEIMFQGEFAVSGKYTVNF<br>SGQAKKRSEDKSVTRTIYTLCEAKLFVELLTELRSCSAASDF<br>DEVVKGYGKDDTRSENGRINAILAKAFNPWVKSFFGDDRRV<br>YKDSRAIYARIAYEMFFRVDPRWKNVDEDVFFMEILGHDDEN<br>TQLHYKQFKLANFSRTWRPEVGDENTRLVALQKLDDEMPGF<br>ARGDAGVRLHETVKQLVEQDPSAKITNSTLRAFKFSPTMISR<br>YLEFAADALGQFVGENGQWQLKIETPAIVLPDEESVETIDEP<br>DDESQDDELDEDEIELDEGGGDEPTEEEGPEEHQPTALKPV<br>FKPAKNNGDGTYKIEFEYDGKHYAWSGPADSPMAAMRSAW<br>ETYYS |
| SEQ ID NO: 3 | TelN target sequence | TATCAGCACACAATTGCCCATTATACGCGCGTATAATGGA<br>CTATTGTGTGCTGATA |
| SEQ ID NO: 4 | AfIII adaptor | TTAAGTAACATTTGTTGGCCACTCAGGCCAACAAATGTTAC |
| SEQ ID NO: 5 | Nhel-HF adaptor | CTAGCTAACATTTGTTGGCCACTCAGGCCAACAAATGTTA<br>G |
| SEQ ID NO: 6 | EcoRV adaptor | TCTAACATTTGTTGGCCACTCAGGCCAACAAATGTTAGAT |
| SEQ ID NO: 7 | Scal adaptor | CTTAACATTTGTTGGCCACTCAGGCCAACAAATGTTAAGT |
| SEQ ID NO: 8 | 5' ITR sequence | CCTGCAGGCAGCTGCGCGCTCGCTCGCTCACTGAGGCCG<br>CCCGGGCAAAGCCCGGGCGTCGGGCGACCTTTGGTCGC<br>CCGGCCTCAGTGAGCGAGCGAGCGCGCAGAGAGGGAGT<br>GGCCAACTCCATCACTAGGGGTTCCT |

TABLE 1-continued

| SEQ ID | Name | Sequence |
|---|---|---|
| SEQ ID NO: 9 | 3' ITR sequence | AGGAACCCCTAGTGATGGAGTTGGCCACTCCCTCTCTGC GCGCTCGCTCGCTCACTGAGGCCGGGCGACCAAAGGTC GCCCGACGCCCGGGCTTTGCCCGGGCGGCCTCAGTGAG CGAGCGAGCGCGCAGCTGCCTGCAGG |

In a particular embodiment of the process of the first aspect of the invention, optionally in combination with any of the embodiments provided above or below, the process comprises the steps of a) providing a DNA template comprising a DNA sequence of interest; b) amplifying DNA from the DNA template of step (a), wherein the amplification comprises the steps of (b.1) priming the DNA template with a primase/polymerase enzyme, and (b.2) elongating the resulting sequence with a polymerase; (c) generating a closed linear DNA with the amplified DNA produced in step (b); and (d) purifying the closed linear DNA produced in step (c).

In a particular embodiment of the process of the first aspect of the invention, optionally in combination with any of the embodiments provided above or below, the primase/polymerase enzyme is selected from TthPrimPol or hsPrimPol. In a particular embodiment, the primase polymerase enzyme is TthPrimPol. In a more particular embodiment, the primase polymerase enzyme is TthPrimPol of SEQ ID NO: 1 or a variant thereof which has a sequence identity of at least 70%, at least 75%, at least 80%, at least 85%, at least 90%, or at least 95% with respect to SEQ ID NO: 1. The skilled in the art would know that any variant of TthPrimPol which maintains its primase activity would be suitable for use in the process of the invention.

In the present invention the term "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=(number of identical positions/total number of positions)×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410. A particular percentage of identity encompasses variations of the sequence due to conservative mutations of one or more amino acids leading to a TthPrimPol enzyme being still effective, thus able to prime suitable sequences. Protein variations are also due to insertions or deletions of one or more amino acids.

In a particular embodiment of the process of the first aspect of the invention, optionally in combination with any of the embodiments provided above or below, the process is an in vitro cell-free process for the production of closed linear DNA.

In a particular embodiment of the process of the first aspect of the invention, optionally in combination with any of the embodiments provided above or below, the amplification of step (b) is a rolling-circle amplification.

The term "rolling-circle amplification" or "RCA" refers to nucleic acid amplification reactions involving the amplification of covalently closed DNA molecules, such as clDNA or double stranded circular DNA, wherein a polymerase performs the extension of a primer around the closed DNA molecule. The polymerase displaces the hybridized copy and continues polynucleotide extension around the template to produce concatameric DNA comprising tandem units of the amplified DNA. These linear single stranded products serve as the basis for multiple hybridization, primer extension and strand displacement events, resulting in formation of concatameric double stranded DNA products. There are thus multiple copies of each amplified single unit DNA in the concatameric double stranded DNA products The skilled in the art knows, making use of their general knowledge and/or the instructions of the manufacturer, how to adjust the conditions of the amplification step depending on the enzymes and the characteristics of the template to be amplified. Depending on how the template DNA is generated, the concatameric DNA will contain different sequences flanking each amplified DNA sequence of interest. For example, in the concatameric DNA the repeated DNA sequence of interest may be flanked by restriction sites, protelomerase target sequences, recombinase recognition sites, or any combination thereof.

In a particular embodiment of the process of the first aspect of the invention, optionally in combination with any of the embodiments provided above or below, the amplification of step (b) is carried out with a strand displacement DNA polymerase. The term "strand-displacement DNA polymerase" refers to a DNA polymerase that that performs a 3' end elongation reaction while removing a double-stranded portion of template DNA. Strand displacement DNA polymerases that can be used in the present invention may not be particularly limited, as long as they have such a strand-displacement activity, such as phi29 DNA polymerase and Bst DNA polymerase. Depending on the thus selected polymerase type, the skilled in the art would know that the reaction conditions for a 3' end elongation reaction may be adequately set. For example, when phi29 DNA polymerase is used, a reaction may be performed at an optimum temperature for the reaction from 25° C. to 35° C.

Thus, in a particular embodiment, the strand displacement DNA polymerase is selected from the group consisting of phi29 DNA polymerase, Bst DNA polymerase, Bca (exo-) DNA polymerase, Klenow fragment of *Escherichia coli* DNA polymerase I, Vent (Exo-) DNA polymerase, Deep-Vent (Exo-) DNA polymerase, and KOD DNA polymerase. In a more particular embodiment, the strand displacement DNA polymerase is phi29 DNA polymerase. In an even more particular embodiment, the strand displacement DNA polymerase is a chimeric protein comprising a phi29 DNA polymerase. The skilled in the art knows how to obtain chimeric DNA polymerases with improved characteristics, for example, as disclosed in WO2011000997.

In a particular embodiment of the process of the first aspect of the invention, optionally in combination with any of the embodiments provided above or below, the DNA template is selected from a closed linear DNA template or a circular double stranded DNA template.

As use herein, the term "circular double stranded DNA" refers to a covalently closed double stranded DNA molecule.

The process for the production of closed linear DNA of the invention may also be performed by priming the amplification of step (b) with random primers.

In a particular embodiment of the process of the first aspect of the invention, optionally in combination with any of the embodiments provided above or below, when the DNA template is a closed linear DNA template, then step (a) is performed by:

contacting a plasmid vector comprising at least two restriction sites flanking the DNA sequence of interest with at least one restriction enzyme thereby producing open double stranded DNA containing the DNA sequence of interest, and attaching single stranded DNA adaptors to both ends of the open double stranded DNA containing the DNA sequence of interest; or, alternatively, it is performed by:

contacting a plasmid vector comprising at least two protelomerase target sequences flanking the DNA sequence of interest with a protelomerase, more particularly, with TelN; thus, obtaining a DNA template which is a closed linear DNA template containing the DNA sequence of interest.

The inventors have surprisingly found that, contrary to what was disclosed in the state of the art, that a primase/polymerase enzyme is capable of priming a clDNA that does not contain adaptors bearing the primase recognition site. In particular, when the clDNA template is generated by the action of a protelomerase, the resulting clDNA presents a structure in which very small single stranded loops are present at the end and said single stranded loops do not contain a protelomerase target sequence. Unexpectedly, the primase/polymerase can prime this type of clDNA allowing the polymerase to start the amplification step, even when the template clDNA is not subjected to denaturing conditions (see FIG. 4).

Thus, in one embodiment of the process of the first aspect of the invention, optionally in combination with any of the embodiments provided above or below, DNA template does not contain a primase/polymerase priming site. In a particular embodiment the DNA template is a clDNA template that does not contain a primase/polymerase priming site.

As used herein, a "plasmid vector" refers to a circular double stranded nucleic acid molecule capable of transporting another nucleic acid to which it has been linked and which is capable of autonomous replication withing a cell independently of the chromosomal DNA. Therefore, plasmid vectors contain all the elements needed for replication in a cell, particularly, in a bacterial cell.

The use of restriction enzymes and ligases (for attaching) is routinary in the field of molecular biology, therefore the skilled in the art would know how to adjust the conditions of the reaction depending on the enzymes used, and which restriction enzyme should be used depending on the restriction site to be targeted.

The skilled in the art also knows that some restriction enzymes generate DNA overhangs (sticky ends) while others do not (blunt ends). Both types of restriction enzymes can be used in the method of the invention. The skilled man knows that an adaptor with sticky ends can be attached to an open double stranded DNA with sticky ends (sticky-end ligation). An open double stranded DNA with blunt ends can also be dA-tailed by a process of adding a terminal 3'deoxy adenosine nucleotide, for instance using Taq polymerase, and then ligated to an adaptor with an overhanging T.

In a particular embodiment of the process of the first aspect of the invention, optionally in combination with any of the embodiments provided above or below, the restriction enzyme generates blunt ends or sticky ends. In a more particular embodiment, the contacting a plasmid vector comprising at least two restriction sites flanking the DNA sequence of interest with at least one restriction enzyme produces open double stranded DNA with sticky ends or open double stranded DNA with blunt ends.

In a particular embodiment of the process of the first aspect of the invention, optionally in combination with any of the embodiments provided above or below, the single stranded DNA adaptors have a hairpin structure. In a more particular embodiment, the single stranded DNA adaptors are of sequence SEQ ID NO: 4, SEQ ID NO: 5, SEQ ID NO: 6, or SEQ ID NO: 7. The adaptors attached to both ends of the open double stranded DNA to form de clDNA can be the same adaptor or different adaptors.

In a particular embodiment of the process of the first aspect of the invention, optionally in combination with any of the embodiments provided above or below, the single stranded DNA adaptors contain one or more, for example at least two, modified nucleotides.

A "modified nucleotide" is any nucleotide (e.g., adenosine, guanosine, cytidine, and thymidine) that has been chemically modified—by modification of the base, the sugar or the phosphate group—or that incorporates a non-natural moiety in its structure. Thus, the modified nucleotide may be naturally or non-naturally occurring depending on the modification.

A modified nucleotide as used herein is preferably a variant of guanosine, uridine, adenosine, thymidine and cytidine including, without implying any limitation, any naturally occurring or non-naturally occurring guanosine, uridine, adenosine, thymidine or cytidine that has been altered chemically, for example by acetylation, methylation, hydroxylation, etc., including 5-methyl-deoxycytidine, 2-amino-deoxyadenosine, 1-methyl-adenosine, 1-methyl-guanosine, 1-methyl-inosine, 2,2-dimethyl-guanosine, 2,6-diaminopurine, 2'-amino-2'-deoxyadenosine, 2'-amino-2'-deoxycytidine, 2'-amino-2'-deoxyguanosine, 2'-amino-2'-deoxyuridine, 2-amino-6-chloropurineriboside, 2-aminopurine-riboside, 2'-araadenosine, 2'-aracytidine, 2'-arauridine, 2'-azido-2'-deoxyadenosine, 2'-azido-2'-deoxycytidine, 2'-azido-2'-deoxyguanosine, 2'-azido-2'-deoxyuridine, 2-chloroadenosine, 2'-fluoro-2'-deoxyadenosine, 2'-fluoro-2'-deoxycytidine, 2'-fluoro-2'-deoxyguanosine, 2'-fluoro-2'-deoxyuridine, 2'-fluorothymidine, 2-methyl-adenosine, 2-methyl-guanosine, 2-methyl-thio-N6-isopenenyl-adenosine, 2'-0-methyl-2-aminoadenosine, 2'-0-methyl-2'-deoxyadenosine, 2'-0-methyl-2'-deoxycytidine, 2'-0-methyl-2'-deoxyguanosine, 2,-0-methyl-2'-deoxyuridine, 2'-0-methyl-5-methyluridine, 2'- 0-methylinosine, 2'-0-methylpseudouridine, 2-thiocytidine, 2-thio-cytidine, 3-methyl-cytidine, 4-acetyl-cytidine, 4-thiouridine, 5-(carboxyhydroxymethyl)-uridine, 5,6-dihydrouridine, 5-aminoallylcytidine, 5-aminoallyl-deoxyuridine, 5-bromouridine, 5-carboxymethylaminomethyl-2-thio-uracil, 5-carboxymethylamonomethyl-uracil, 5-chloro-ara-cytosine, 5-fluoro-uridine, 5-iodouridine, 5-methoxycarbonylmethyl-uridine, 5-methoxy-uridine, 5-methyl-2-thio-uridine, 6-Azacytidine, 6-azauridine, 6-chloro-7-deaza-guanosine, 6-chloropurineriboside, 6-mercapto-guanosine, 6-methyl-mercaptopurine-riboside, 7-deaza- 2'-deoxy-guanosine, 7-deazaadenosine, 7-methyl-guanosine, 8-azaadenosine, 8-bromo-adenosine, 8-bromo-guanosine, 8-mercapto-guanosine, 8-oxoguanosine, benzimidazole-riboside, beta-D-mannosyl-queosine, dihydro-uridine, inosine, N1-methyladenosine, N6-([6-aminohexyl]carbamoylmethyl)-adenosine, N6-isopentenyl-adenosine, N6-methyl-adenosine, N7-methyl-xanthosine, N-uracil-5-oxyacetic acid methyl ester, puromycin, queosine, uracil-5-oxyacetic acid, uracil-5-oxyacetic acid methyl ester, wybutoxosine, xanthosine, and xylo-adenosine. The preparation of such variants is known to the person skilled in the art, for example from U.S. Pat. No. 4,373,071.

The modified nucleotides may also include, without limitation pyridin-4-oneribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine, 5-aza-cytidine, pseudoisocytidine, 3-methyl-cytidine, N4-acetyl-cytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

The modified nucleotides may also include, without limitation 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

The modified nucleotides may also include, without limitation inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The modified nucleotides may also include, without limitation 6-aza-cytidine, 2-thio-cytidine, alpha-thio-cytidine, pseudo-iso-cytidine, 5-aminoallyl-uridine, 5-iodo-uridine, N1-methyl-pseudouridine, 5,6-dihydrouridine, alpha-thio-uridine, 4-thio-uridine, 6-aza-uridine, 5-hydroxy-uridine, deoxy-thymidine, 5-methyl-uridine, pyrrolo-cytidine, inosine, alpha-thio-guanosine, 6-methyl-guanosine, 5-methyl-cytdine, 8-oxo-guanosine, 7-deaza-guanosine, N1-methyl-adenosine, 2-amino-6-chloro-purine, N6-methyl-2-amino-purine, pseudo-iso-cytidine, 6-chloro-purine, N6-methyl-adenosine, alpha-thio-adenosine, 8-azido-adenosine, 7-deaza-adenosine.

The modified nucleotide may be chemically modified at the 2' position. Preferably, the modified nucleotide comprises a substituent at the 2' carbon atom, wherein the substituent is selected from the group consisting of a halogen, an alkoxy group, a hydrogen, an aryloxy group, an amino group and an aminoalkoxy group, preferably from 2'-hydrogen (2'-deoxy), 2'-0-methyl, 2'-0-methoxyethyl and 2'-fluoro.

Another chemical modification that involves the 2' position of a nucleotide as described herein is a locked nucleic acid (LNA) nucleotide, an ethylene bridged nucleic acid (ENA) nucleotide and an (S)-constrained ethyl cEt nucleotide. These backbone modifications lock the sugar of the modified nucleotide into the preferred northern conformation. The phosphate groups of the backbone can be modified, for example, by replacing one or more of the oxygen atoms with a different substituent. Further, the modified nucleotide can include the full replacement of an unmodified phosphate moiety with a modified phosphate as described herein. Examples of modified phosphate groups include, but are not limited to, the group consisting of a phosphorothioate (also known as tiophosphate), a phosphoroselenate, a borano phosphate, a borano phosphate ester, a hydrogen phosphonate, a phosphoroamidate, an alkyl phosphonate, an aryl phosphonate and a phosphotriester. The phosphate linker can also be modified by the replacement of a linking oxygen with nitrogen (bridged phosphoroamidates), sulfur (bridged phosphorothioates) and carbon (bridged methylene-phosphonates).

The modified nucleotide may be an abasic site. As used herein, an "abasic site" is a nucleotide lacking the organic base. In preferred embodiments, the abasic nucleotide further comprises a chemical modification as described herein at the 2' position of the ribose. Preferably, the 2' C atom of the ribose is substituted with a substituent selected from the group consisting of a halogen, an alkoxy group, a hydrogen, an aryloxy group, an amino group and an aminoalkoxy group, preferably from 2'-hydrogen (2'-deoxy), 2'-0-methyl, 2'-0-methoxyethyl and 2'-fluoro.

In a particular embodiment of the first aspect of the invention, optionally in combination with any of the embodiments provided above or below, the at least two modified nucleotides are independently selected form the group consisting of 2-amino-deoxyadenosine, 5-methyl-deoxycytidine, thiophosphate nucleotide, LNA nucleotide, Inosine, 8-oxo-deoxyAdenosine and 5-fluoro-deoxyuracil and L-DNA nucleotide.

In a particular embodiment of the first aspect of the invention, optionally in combination with any of the embodiments provided above or below, the at least two modified nucleotides are not L-DNA nucleotide, 5-bromouridine or 5-iodouridine.

2-amino-deoxyadenosine (also known as 2-Amino-2'-deoxyadenosine or 2-Amino-dA) is a derivate from deoxyadenosine. 2-amino-deoxyadenosine has the IUPAC name (2R,3S,5R)-5-(2,6-diaminopurin-9-yl)-2-(hydroxymethyl)oxolan-3-ol, and the CAS number 4546-70-7.

5-methyl-deoxycytidine (5-Methyl-dCTP), is a derivate from deoxycytidine, which as a IUPAC name ([[(2R,3S,5R)-5-(4-amino-5-methyl-2-oxopyrimidin-1-yl)-3-hydroxyoxolan-2-yl]methoxy-hydroxyphosphoryl] phosphono hydrogen phosphate, and the CAS number 22003-12-9.

A thiophosphate nucleotide is any nucleotide that contains a thiophosphate (also known as phosphorothioate) as phosphate group. Thiophosphate has a CAS number 15181-41-6.

An LNA nucleotide is a modified RNA nucleotide in which the ribose moiety is modified with an extra bridge connecting the 2' oxygen and 4' carbon.

An L-DNA nucleotide refers to a nucleotide that contains the L enantiomer of the ribose or deoxyribose.

In a more particular embodiment of the first aspect of the invention, optionally in combination with any of the embodiments provided above or below, the clDNA comprises at least three, at least four, or at least five modified nucleotides independently selected form the group consisting of thiophosphate, locked nucleic acid, 2,6-diaminopurine, 5-methyl-deoxycytidine, Inosine, 8-oxo-deoxyAdenosine and 5-fluoro-deoxyuracil and L-DNA nucleotide.

In a more particular embodiment of the first aspect of the invention, optionally in combination with any of the embodiments provided above or below, the clDNA comprises two LNA nucleotides.

In a particular embodiment of the process of the first aspect of the invention, optionally in combination with any of the embodiments provided above or below, the single stranded DNA adaptors comprise at least one restriction site. In a more particular embodiment, the restriction site is selected from the group consisting of a BsaI restriction site, AflII restriction site, HindIII restriction site, NheI restriction site, and EcoRV restriction site. In an even more particular embodiment, the restriction site is a BsaI restriction site.

In a particular embodiment of the process of the first aspect of the invention, optionally in combination with any of the embodiments provided above or below, the single stranded DNA adaptors do not contain a primase recognition site. In a more particular embodiment, the single stranded DNA adaptors do not contain the sequence XTC.

In a more particular embodiment of the process of the first aspect of the invention, optionally in combination with any of the embodiments provided above or below, when the DNA template is a closed linear DNA template, then step (a) is performed by:

contacting a plasmid vector comprising at least two restriction sites flanking the DNA sequence of interest with at least one restriction enzyme thereby producing open double stranded DNA containing the DNA sequence of interest, and attaching single stranded DNA adaptors to both ends of the open double stranded DNA containing the DNA sequence of interest, with the proviso that the single stranded DNA adaptors do not contain a primase/polymerase priming site; or, alternatively, it is performed by:

contacting a plasmid vector comprising at least two protelomerase target sequences flanking the DNA sequence of interest with a protelomerase, more particularly, with TelN; thus, obtaining a DNA template which is a closed linear DNA template containing the DNA sequence of interest. In a more particular embodiment, the single stranded DNA adaptors do not contain the sequence XTC.

In a more particular embodiment, optionally in combination with any of the embodiments provided above or below, the single stranded DNA adaptors contain a protelomerase target sequence. In another particular embodiment, optionally in combination with any of the embodiments provided above or below, the single stranded DNA adaptors do not contain a protelomerase target sequence. In another particular embodiment, the single stranded DNA adaptors contain a portion of a protelomerase target sequence, wherein said portion of a protelomerase target sequence is not recognized by protelomerase. As used herein, "protelomerase" is any polypeptide capable of cleaving and rejoining a template comprising a protelomerase target site in order to produce a covalently closed linear DNA molecule. Thus, the protelomerase has DNA cleavage and ligation functions. Enzymes having protelomerase-type activity have also been described as telomere resolvases (for example in *Borrelia burgdorferi*). A typical substrate for protelomerase is circular double stranded DNA. If this DNA contains a protelomerase target site, the enzyme can cut the DNA at this site and ligate the ends to create a linear double stranded covalently closed DNA molecule. The ability of a given polypeptide to catalyze the production of closed linear DNA from a template comprising a protelomerase target site can be determined using any suitable assay described in the art.

Examples of suitable protelomerases for use in the process of the invention include those from bacteriophages such as phiHAP-1 from *Halomonas aquamarina,* PY54 from *Yersinia enterolytica,* phiKO2 from *Klebsiella oxytoca* and VP882 from *Vibrio* sp., and N15 from *Escherichia coli,* or variants of any thereof.

In a particular embodiment of the process of the first aspect of the invention, optionally in combination with any of the embodiments provided above or below, the protelomerase is bacteriophage N15 TelN of SEQ ID NO: 2 or a variant thereof which comprises a sequence having at least 80% identity, at least 85% identity, at least 90% identity, or at least 95% identity to SEQ ID NO: 2.

A "protelomerase target sequence" is any DNA sequence whose presence in a DNA template allows for its conversion into a closed linear DNA by the enzymatic activity of protelomerase. In other words, the protelomerase target sequence is required for the cleavage and re-ligation of double stranded DNA by protelomerase to form covalently closed linear DNA. Typically, a protelomerase target sequence comprises any perfect palindromic sequence i.e. any double-stranded DNA sequence having two-fold rotational symmetry, also described herein as a perfect inverted repeat.

In a particular embodiment of the process of the first aspect of the invention, optionally in combination with any of the embodiments provided above or below, at least two protelomerase target sequences comprises a perfect inverted repeat DNA sequence.

In a particular embodiment of the process of the first aspect of the invention, optionally in combination with any of the embodiments provided above or below, the protelomerase target sequence comprises the sequence of SEQ ID NO: 3 or a variant thereof which comprises a sequence having at sequence identity of at least 80%, at least 85%, at least 90%, or at least 95% sequence identity with respect to SEQ ID NO: 3.

The length of the perfect inverted repeat differs depending on the specific organism. In *Borrelia burgdorferi,* the perfect inverted repeat is 14 base pairs in length. In various mesophilic bacteriophages, the perfect inverted repeat is 22 base pairs or greater in length. Also, in some cases, e.g. *E. coli* N15, the central perfect inverted palindrome is flanked by inverted repeat sequences, i.e. forming part of a larger imperfect inverted palindrome.

A protelomerase target sequence as used in the invention preferably comprises a double stranded palindromic (perfect inverted repeat) sequence of at least 14 base pairs in length.

The perfect inverted repeat may be flanked by additional inverted repeat sequences. The flanking inverted repeats may be perfect or imperfect repeats i.e. may be completely symmetrical or partially symmetrical. The flanking inverted repeats may be contiguous with or non-contiguous with the central palindrome. The protelomerase target sequence may comprise an imperfect inverted repeat sequence which comprises a perfect inverted repeat sequence of at least 14 base pairs in length A protelomerase target sequence comprising the sequence of SEQ ID NO: 3 or a variant thereof is preferred for use in combination with *E. coli* N15 TelN protelomerase of SEQ ID NO: 2 and variants thereof.

Variants of any of the palindrome or protelomerase target sequences described above include homologues or mutants thereof. Mutants include truncations, substitutions or deletions with respect to the native sequence. A variant sequence is any sequence whose presence in the DNA template allows for its conversion into a closed linear DNA by the enzymatic activity of protelomerase. This can readily be determined by use of an appropriate assay for the formation of closed linear DNA. Any suitable assay described in the art may be used. Preferably, the variant allows for protelomerase binding and activity that is comparable to that observed with the native sequence. Examples of preferred variants of palindrome sequences described herein include truncated palindrome sequences that preserve the perfect repeat structure, and remain capable of allowing for formation of closed linear DNA. However, variant protelomerase target sequences may be modified such that they no longer preserve a perfect palindrome, provided that they are able to act as substrates for protelomerase activity.

It should be understood that the skilled person would readily be able to identify suitable protelomerase target sequences for use in the invention on the basis of the structural principles outlined above. Candidate protelomerase target sequences can be screened for their ability to promote formation of closed linear DNA using the assays described above.

In a particular embodiment of the process of the first aspect of the invention, optionally in combination with any of the embodiments provided above or below, when the DNA template is a circular double stranded DNA template containing the DNA sequence of interest, then step (a) is performed by contacting a plasmid vector comprising at least two recombinase recognition sites flanking the DNA sequence of interest with a site-specific recombinase, more particularly, a Cre recombinase.

The action of the site-specific recombinase on the plasmid vector triggers the recombination of the two recombinase recognition sites thereby generating a smaller circular double stranded DNA that contains the DNA sequence of interest that was located between the recombinase recognition sites in the plasmid vector.

"Site-specific recombinase" as used herein refers to a family of enzymes that mediate the site-specific recombination between specific DNA sequences recognized by the enzymes known as recombinase recognition sites. Examples of site-specific recombinases include, without limitation, Cre recombinase, Flp recombinase, the lambda integrase, gamma-delta resolvase, Tn3 resolvase, Sin resolvase, Gin invertase, Hin invertase, Tn5044 resolvase, Tn3 transposase, sleeping beauty transposase, IS607 transposase, Bxb I integrase, wBeta integrase, BL3 integrase, phiR4 integrase, Al I 8 integrase, TGI integrase, MRU integrase, phi370 integrase, SPBc integrase, SV1 integrase, TP901-1 integrase, phiRV integrase, FC1 integrase, K38 integrase, phiBTI integrase and phiC31 integrase.

"Recombinase recognition sites" refers to nucleotide sequences that are recognized by a site-specific recombinase and can serve as a substrate for a recombination event. Non-limiting examples of recombinase recognition sites include FRT, FRT11, FRT71, attp, att, rox, and lox sites such as loxP, lox511, 1oX2272, 1oX66, 1oX71, loxM2, and lox5171.

The skilled in the art would know, using his common general knowledge, that each site-specific recombinase recognizes a particular recombinase recognition site, thus depending on the recognition sequence contained in the plasmid vector a different recombinase should be used for generating the circular double stranded DNA template from the plasmid vector.

In a particular embodiment of the process of the first aspect of the invention, optionally in combination with any of the embodiments provided above or below, the site-specific recombinase is Cre recombinase. In a more particular embodiment, the recombinase recognition site is loxP. In an even more particular embodiment, the site-specific recombinase is Cre recombinase and the recombinase recognition site is loxP.

Depending on the sequences flanking the DNA sequence of interest on the plasmid vector, and the process used to generate the DNA template in step (a), the concatemeric products produced in step (b) will comprise the DNA sequence of interest flanked by a different sequence. For instance, if the DNA sequence of interest is only flanked by protelomerase target sequences in the plasmid vector, the DNA sequence of interest in the concatemeric DNA will be flanked by said protelomerase target sequences. Moreover, the DNA sequence of interest in the plasmid vector can be flanked by combinations of different sequences to allow the production of the DNA template by one type of reaction (for example, by TelN), and then allow the generation of the clDNA from the amplification products by another reaction (for instance, restriction enzyme digestion and adaptor ligations). In this particular case, the DNA sequence of interest should be flanked by restriction sites, which in turn are flanked by protelomerase target sites.

Thus, in a particular embodiment of the process of the first aspect of the invention, optionally in combination with any of the embodiments provided above or below, wherein the amplified DNA resulting from step (b) is a concatameric DNA comprising repeats of the DNA sequence of interest, wherein each one of the repeated DNA sequences of interest is flanked by restriction sites, protelomerase target sequences, and/or recombinase recognition sites.

The skilled in the art would know that the excision of the tandem units of the DNA sequence of interest in the form of closed linear DNA can be performed by different routinary molecular biology techniques that allow to cut of the tandem units and closure of the open ends of the fragments to form a covalently closed molecule. These two steps can be performed subsequently, for instance by restriction enzyme digestion and adapter ligation, or simultaneously, by the action of a protelomerase.

In a particular embodiment of the process of the first aspect of the invention, optionally in combination with any of the embodiments provided above or below, when the concatameric DNA comprises repeats of the DNA sequence of interest flanked by at least restriction sites, then step (c) is performed by: (c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments. All the embodiments above provided regarding restriction enzymes, restriction sites, and single stranded DNA adaptors are also meant to apply to this embodiment. Moreover, the skilled in the art would know that if a restriction enzyme is used to produce the template clDNA, the same restriction enzyme can be later used to generate clDNA from the amplified DNA produced in step (b). The single stranded DNA adaptors used in step (a) for generating the template clDNA can be same or different to the ones used in step (c).

In a particular embodiment of the process of the first aspect of the invention, optionally in combination with any of the embodiments provided above or below, when the concatameric DNA comprises repeats of the DNA sequence of interest flanked by at least protelomerase target sequences, then step (c) is performed by contacting the concatameric DNA with a protelomerase, more particularly, with TelN. All the embodiments above provided regarding protelomerases and protelomerase target sites are also meant to apply to this embodiment. Moreover, the skilled in the art would know that if a protelomerase is used to produce the template clDNA in step (a), the same protelomerase can be later used in step (c) to generate clDNA from the amplified DNA.

In a particular embodiment of the process of the first aspect of the invention, optionally in combination with any of the embodiments provided above or below, the process is for the production of a closed linear expression cassette DNA.

In a particular embodiment of the process of the first aspect of the invention, optionally in combination with any of the embodiments provided above or below, step (a) is performed by contacting a plasmid vector comprising at least two restriction sites flanking the DNA sequence of interest with at least one restriction enzyme thereby producing open double stranded DNA containing the DNA sequence of interest, and attaching single stranded DNA adaptors to both ends of the open double stranded DNA containing the DNA sequence of interest; and step (c) is performed by (c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments. In a more particular embodiment, the restriction enzyme generates sticky ends or blunt ends. When the restriction enzyme generates blunt ends, the resulting fragment can be attached to adaptors containing blunt ends or alternatively it can be dA-tailed, as explained above, and then attached to an adaptor with an overhanging T.

In a particular embodiment of the process of the first aspect of the invention, optionally in combination with any of the embodiments provided above or below, step (a) is performed by contacting a plasmid vector comprising at least two restriction sites flanking at least two protelomerase recognition sites flanking the DNA sequence of interest, with at least one restriction enzyme thereby producing open double stranded DNA containing the DNA sequence of interest flanked by protelomerase recognition sequences, and attaching single stranded DNA adaptors to both ends of the open double stranded DNA; and step (c) is performed by contacting the concatameric DNA with a protelomerase, more particularly, with TelN.

In a particular embodiment of the process of the first aspect of the invention, optionally in combination with any of the embodiments provided above or below, when the DNA template is a circular double stranded DNA template containing the DNA sequence of interest flanked by restriction sites, then step (a) is performed by contacting a plasmid vector comprising at least two recombinase recognition sites flanking at least two restriction sites flanking the DNA sequence of interest with a site-specific recombinase, more particularly, a Cre recombinase; and step (c) is performed by (c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments.

In a particular embodiment of the process of the first aspect of the invention, optionally in combination with any of the embodiments provided above or below, when the DNA template is a circular double stranded DNA template containing the DNA sequence of interest flanked by restriction sites, then step (a) is performed by contacting a plasmid vector comprising at least two recombinase recognition sites flanking at least two restriction sites flanking the DNA sequence of interest with a site-specific recombinase, more particularly, a Cre recombinase; and step (c) is performed by contacting the concatameric DNA with a protelomerase, more particularly, with TelN.

In a particular embodiment of the process of the first aspect of the invention, optionally in combination with any of the embodiments provided above or below, step (a) is performed by contacting a plasmid vector comprising at least two protelomerase target sequences flanking at least two restriction sites flanking the DNA sequence of interest with a protelomerase, more particularly, with TelN; and step (c) is performed by (c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments.

In a particular embodiment of the process of the first aspect of the invention, optionally in combination with any of the embodiments provided above or below, step (a) is performed by contacting a plasmid vector comprising two protelomerase target sequences flanking at least two restriction sites flanking the DNA sequence of interest with a protelomerase, for example, with TelN; and step (c) is performed by (c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments.

In a particular embodiment of the process of the first aspect of the invention, optionally in combination with any of the embodiments provided above or below, step (a) is performed by contacting a plasmid vector comprising at least two protelomerase target sequences (e.g. for protelomerase A) flanking at least two protelomerase recognition sites different from the first (e.g. for protelomerase B) flanking the DNA sequence of interest, with a corresponding protelomerase (e.g. for protelomerase A); and step (c) is performed by contacting the concatameric DNA with a corresponding protelomerase (e.g. for protelomerase B). In a particular embodiment the protelomerase in step (a) or in step (c) is TelN.

In a particular embodiment of the process of the first aspect of the invention, optionally in combination with any of the embodiments provided above or below, step (a) is performed by contacting a plasmid vector comprising two protelomerase target sites flanking the DNA sequence of interest, with a protelomerase; and step (c) is performed by contacting the concatameric DNA with a protelomerase. In a particular embodiment the protelomerase in step (a) or in step (c) is TelN.

In a particular embodiment of the process of the first aspect of the invention, optionally in combination with any of the embodiments provided above or below, step (a) is performed by contacting a plasmid vector comprising at least two restriction sites flanking the DNA sequence of interest and no protelomerase target sites with at least one restriction enzyme thereby producing open double stranded DNA containing the DNA sequence of interest, and attaching single stranded DNA adaptors to both ends of the open double stranded DNA containing the DNA sequence of interest, with the proviso that the single stranded DNA adaptors do not contain protelomerase target sites; and step (c) is performed by (c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments.

In a particular embodiment of the process of the first aspect of the invention, optionally in combination with any of the embodiments provided above or below, the DNA sequence of interest comprises an expression cassette. In a more particular embodiment, the expression cassette consists of a eukaryotic promoter operably linked to a sequence encoding a protein of interest, and optionally an enhancer and/or a eukaryotic transcription termination sequence.

The term “expression cassette” refers to a DNA sequence comprising one or more promoter or enhancer elements and a gene or other coding sequence which encodes an mRNA, miRNA, siRNA or protein of interest. The expression cassette may further comprise other elements that regulate the expression of the coding sequence, such as a transcription termination site.

In a particular embodiment of the process of the first aspect of the invention, optionally in combination with any of the embodiments provided above or below, the DNA sequence of interest comprises an expression cassette flanked by inverted terminal repeats (ITRs). The ITRs can be at any suitable distance from the expression cassette, for instance, the ITRs can be directly linked to the expression cassette or at a distance from 1 to 50 nucleotides, from 50 to 200 nucleotides, from 200 to 1000 nucleotides. Thus, in a particular embodiment, optionally in combination with any of the embodiments provided above or below, the DNA of interest comprises an expression cassette flanked by inverted terminal repeats (ITRs) at a distance from 1 to 50 nucleotides.

As used herein, the term “terminal repeat” or “TR” includes any viral terminal repeat or synthetic sequence that comprises at least one minimal required origin of replication and a region comprising a palindrome hairpin structure. A Rep-binding sequence (“RBS”) (also referred to as RBE (Rep-binding element)) and a terminal resolution site (“TRS”) together constitute a “minimal required origin of replication” and thus the TR comprises at least one RBS and at least one TRS. TRs that are the inverse complement of one another within a given stretch of polynucleotide sequence are typically each referred to as an “inverted terminal repeat” or “ITR”. In the context of a virus, ITRs mediate replication, virus packaging, integration and provirus rescue.

It will be understood by one of ordinary skill in the art that in complex clDNA configurations more than two ITRs or asymmetric ITR pairs may be present. The ITR can be an AAV ITR or a non-AAV ITR, or can be derived from an AAV ITR or a non-AAV ITR. For example, the ITR can be derived from the family Parvoviridae, which encompasses parvoviruses and dependoviruses (e.g., canine parvovirus, bovine parvovirus, mouse parvovirus, porcine parvovirus, human parvovirus B-19), or the SV40 hairpin that serves as the origin of SV40 replication can be used as an ITR, which can further be modified by truncation, substitution, deletion, insertion and/or addition. Parvoviridae family viruses consist of two subfamilies: Parvovirinae, which infect vertebrates, and Densovirinae, which infect invertebrates. Dependoparvoviruses include the viral family of the adeno-associated viruses (AAV) which are capable of replication in vertebrate hosts including, but not limited to, human, primate, bovine, canine, equine and ovine species. For convenience herein, an ITR located 5' to (upstream of) an expression cassette in a clDNA vector is referred to as a"5' ITR" or a “left ITR”, and an ITR located 3' to (downstream of) an expression cassette in a clDNA vector is referred to as a"3' ITR" or a “right ITR”.

In a particular embodiment of the process of the first aspect of the invention, optionally in combination with any of the embodiments provided above or below, the DNA sequence of interest comprises an expression cassette flanked by at least one inverted terminal repeat of sequence SEQ ID NO: 8 or SEQ ID NO: 9.

In a particular embodiment of the process of the first aspect of the invention, optionally in combination with any of the embodiments provided above or below, the DNA sequence of interest comprises an expression cassette flanked by a 5' inverted terminal repeat of sequence SEQ ID NO: 8 and/or a 3' inverted terminal repeat of sequence SEQ ID NO: 9.

In a particular embodiment of the process of the first aspect of the invention, optionally in combination with any of the embodiments provided above or below, the DNA sequence of interest comprises an expression cassette flanked by at least one DD-ITR. “DD-ITR” refers to an ITR with flanking D elements as disclosed in Xiao X. et al., “A novel 165-base-pair terminal repeat sequence is the sole cis requirement for the adeno-associated virus life cycle”, 1997, J Virol., vol. 71(2), pp. 941-948.

Regarding the step (d) of the method where the produced clDNAs are purified, the skilled in the art knows that any known method suitable for purifying nucleic acids, in particular clDNAs, could be used.

As mentioned above, in a second aspect the invention provides a closed linear DNA obtainable according to the process as defined in the first aspect.

For the purposes of the invention the expressions "obtainable", "obtained" and equivalent expressions are used interchangeably, and in any case, the expression "obtainable" encompasses the expression "obtained". All the embodiments provided under the first aspect of the invention are also embodiments of the closed linear DNA of the second aspect of the invention.

In a particular embodiment of the second aspect of the invention, optionally in combination with any of the embodiments provided above or below, the closed linear DNA comprises one or more expression cassettes.

In a particular embodiment of the second aspect of the invention, optionally in combination with any of the embodiments provided above or below, the expression cassette comprises a eukaryotic promoter operably linked to a sequence encoding an mRNA, miRNA, siRNA or protein.

In a particular embodiment of the second aspect of the invention, optionally in combination with any of the embodiments provided above or below, the expression cassette further comprises a eukaryotic transcription termination sequence.

In a particular embodiment of the second aspect of the invention, optionally in combination with any of the embodiments provided above or below, the expression cassette lacks one or more bacterial or vector sequences selected from the group consisting of:

(i) bacterial origins of replication;
(ii) bacterial selection markers; and
(iii) unmethylated CpG motifs.

In a particular embodiment of the second aspect of the invention, optionally in combination with any of the embodiments provided above or below, the DNA sequence of interest comprises an expression cassette flanked by inverted terminal repeats (ITRs).

As mentioned before, the invention also provides in a third aspect the closed linear DNA according to the first aspect for use in therapy.

The clDNA of the invention may be used for in vitro expression in a host cell, particularly in DNA vaccines or gene therapy. DNA vaccines typically encode a modified form of an infectious organism's DNA. DNA vaccines are administered to a subject where they then express the selected protein of the infectious organism, initiating an immune response against that protein which is typically protective. DNA vaccines may also encode a tumor antigen in a cancer immunotherapy approach.

A DNA vaccine may comprise a nucleic acid sequence encoding an antigen for the treatment or prevention of a number of conditions including but not limited to cancer, allergies, toxicity and infection by a pathogen such as, but not limited to, fungi, viruses including Human Papilloma Viruses (HPV), HIV, HSV2/HSV1, Influenza virus (types A, B and C), Polio virus, RSV virus, Rhinoviruses, Rotaviruses, Hepatitis A virus, Norwalk Virus Group, Enteroviruses, Astroviruses, Measles virus, Parainfluenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; bacteria including *Mycobacterium tuberculosis, Chlamydia, Neisseria gonorrhoeae, Shigella, Salmonella, Vibrio cholerae, Treponema pallidum, Pseudomonas, Bordetella pertussis, Brucella, Franciscella tularensis, Helicobacter pylori, Leptospira interrogans, Legionella pneumophila, Yersinia pestis, Streptococcus* (types A and B), Pneumococcus, Meningococcus, *Haemophilus influenza* (type b), Toxoplasma gondii, Campylobacteriosis, *Moraxella catarrhalis,* Donovanosis, and Actinomycosis; fungal pathogens including Candidiasis and Aspergillosis; parasitic pathogens including Taenia, Flukes, Roundworms, Amoebiasis, Giardiasis, Cryptosporidium, Schistosoma, Pneumocystis carinii, Trichomoniasis and Trichinosis.

DNA vaccines may comprise a nucleic acid sequence encoding an antigen from a member of the adenoviridae (including for instance a human adenovirus), herpesviridae (including for instance HSV-1, HSV-2, EBV, CMV and VZV), papovaviridae (including for instance HPV), poxviridae (including for instance smallpox and vaccinia), parvoviridae (including for instance parvovirus B19), reoviridae (including for instance a rotavirus), coronaviridae (including for instance SARS), flaviviridae (including for instance yellow fever, West Nile virus, dengue, hepatitis C and tick-borne encephalitis), picornaviridae (including polio, rhinovirus, and hepatitis A), togaviridae (including for instance rubella virus), filoviridae (including for instance Marburg and Ebola), paramyxoviridae (including for instance a parainfluenza virus, respiratory syncitial virus, mumps and measles), rhabdoviridae (including for instance rabies virus), bunyaviridae (including for instance Hantaan virus), orthomyxoviridae (including for instance influenza A, B and C viruses), retroviridae (including for instance HIV and HTLV) and hepadnaviridae (including for instance hepatitis B).

The antigen may be from a pathogen responsible for a veterinary disease and in particular may be from a viral pathogen, including, for instance, a Reovirus (such as African Horse sickness or Bluetongue virus) and Herpes viruses (including equine herpes). The antigen may be one from Foot and Mouth Disease virus, Tick borne encephalitis virus, dengue virus, SARS, West Nile virus and Hantaan virus. The antigen may be from an immunodeficiency virus, and may, for example, be from SIV or a feline immunodeficiency virus.

clDNAs produced by the process of the invention may also comprise a nucleic acid sequence encoding tumour antigens. Examples of tumour associated antigens include, but are not limited to, cancer-testes antigens such as members of the MAGE family (MAGE 1, 2, 3 etc), NY-ESO-1 and SSX-2, differentiation antigens such as tyrosinase, gp100, PSA, Her-2 and CEA, mutated self-antigens and viral tumour antigens such as E6 and/or E7 from oncogenic HPV types. Further examples of particular tumour antigens include MART-1, Melan-A, p97, beta-HCG, GalNAc, MAGE-1, MAGE-2, MAGE-4, MAGE-12, MUC1, MUC2, MUC3, MUC4, MUC18, CEA, DDC, P1A, EpCam, melanoma antigen gp75, Hker 8, high molecular weight melanoma antigen, K19, Tyr1, Tyr2, members of the pMel 17 gene family, c-Met, PSM (prostate mucin antigen), PSMA (prostate specific membrane antigen), prostate secretary protein, alpha-fetoprotein, CA125, CA19.9, TAG-72, BRCA-1 and BRCA-2 antigen.

Also, the process of the invention may produce other types of therapeutic clDNA e.g. those used in gene therapy. For example, such DNA molecules can be used to express a functional gene where a subject has a genetic disorder caused by a dysfunctional version of that gene. Examples of such diseases include Duchenne muscular dystrophy, cystic fibrosis, Gaucher's Disease, and adenosine deaminase (ADA) deficiency. Other diseases where gene therapy may be useful include inflammatory diseases, autoimmune, chronic and infectious diseases, including such disorders as AIDS, cancer, neurological diseases, cardivascular disease, hypercholestemia, various blood disorders including various anaemias, thalassemia and haemophilia, and emphysema. For the treatment of solid tumors, genes encoding toxic peptides (i.e., chemotherapeutic agents such as ricin, diptheria toxin and cobra venom factor), tumor suppressor genes such as p53, genes coding for mRNA sequences which are antisense to transforming oncogenes, antineoplastic peptides such as tumor necrosis factor (TNF) and other cytokines, or transdominant negative mutants of transforming oncogenes, may be expressed.

Other types of therapeutic clDNA are also contemplated for production by the process of the invention. For example, clDNAs which are transcribed into an active RNA form, for example a small interfering RNA (siRNA) may be produced according to the process of the invention.

As mentioned above, the invention also provides a pharmaceutical composition comprising a therapeutically effective amount of the closed linear DNA according to the second aspect of the invention and pharmaceutically acceptable carriers or excipients.

The expression "therapeutically effective amount" as used herein, refers to the amount of the clDNA that, when administered, is sufficient to prevent development of, or alleviate to some extent, one or more of the symptoms of the disease which is addressed. The particular dose of agent administered according to this invention will of course be determined by the particular circumstances surrounding the case, including the clDNA administered, the route of administration, the particular condition being treated, and the similar considerations.

The expression "pharmaceutical composition" encompasses both compositions intended for human as well as for non-human animals (i.e. veterinarian compositions).

The expression "pharmaceutically acceptable carriers or excipients" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the closed linear DNA, the pharmaceutically acceptable excipients, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as coloring agents, coating agents, sweetening, and flavouring agents can be present in the composition, according to the judgment of the formulator.

The pharmaceutical compositions containing the closed linear DNA produced according to the process of the invention can be presented in any dosage form, for example, solid or liquid, and can be administered by any suitable route, for example, oral, parenteral, rectal, topical, intranasal or sublingual route, for which they will include the pharmaceutically acceptable excipients necessary for the formulation of the desired dosage form, for example, topical formulations (ointment, creams, lipogel, hydrogel, etc.), eye drops, aerosol sprays, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding excipients include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

As above disclosed, the invention provides in a fifth aspect a concatameric DNA comprising repeats of a DNA sequence of interest, wherein each one of the repeated DNA sequence of interest is flanked by at least recombinase recognition sites or, alternatively, by at least restriction sites and protelomerase target sequences.

In a particular embodiment of the fifth aspect of the invention, optionally in combination with any of the embodiments provided above or below, each one of the repeated DNA sequences of interest is additionally flanked by ITRs.

In a particular embodiment of the fifth aspect of the invention, optionally in combination with any of the embodiments provided above or below, the concatameric DNA comprises ten or more repeats of the DNA sequence of interest.

In a particular embodiment of the fifth aspect of the invention, optionally in combination with any of the embodiments provided above or below, the concatameric DNA is at least 5 kb in size.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim and shall not be construed as limiting the scope of the claim. Furthermore, the present invention covers all possible combinations of particular and preferred embodiments described herein.

EXAMPLES

Example 1: TthPrimPol Based Amplification of a DNA Template Provides Higher Sequence Fidelity than Random Primers RCA amplification of 10 ng of the plasmid vector containing a DNA sequence of interest ( pUC57-Kan_TELO-CMVEGFP having SEQ ID NO: 23) was carried out by phi29 primed either by TthPrimPol or random primers (RPs). The reaction conditions were 6 h at 30° C. and 10 min at 65° C. in a total reaction volume of 100 μl.

As shown in FIG. 1, the amplification primed with TthPrimPol did not generate any amplification product in the absence of the DNA template (left columns, NTC). On the other hand, the amplification primed with RPs produced a high DNA yield even in the absence of DNA template, suggesting that TthPrimPol priming provides highly specific amplification reactions. Moreover, the DNA yield produced by TthPrimPol priming was in the same order of magnitude as the DNA yield produced by RPs in the presence of a DNA template (right columns, Plasmid).

Finally, amplification products primer by either TthPrimPol or RPs were purified and sequence using Illumina technology (5 million read pairs 2×150 bps) using standard protocols. As shown in FIG. 2, bioinformatic analysis of the sequencing results showed that TthPrimPol-based amplification was able to produce 80% of usable reads, whereas the amplification with random synthetic primers produced only 66% usable reads, confirming the generation of less DNA artefacts when the priming method is based on the use of TthPrimPol.

In conclusion, the results above suggest that the use of TthPrimPol in processes for the production of therapeutic polynucleotides could be advantageous due the higher fidelity it imparts on the amplification step.

Example 2: Production of clDNA Based on TthPrimPol Primed Amplification 10 ng of the plasmid pUC57-Kan_TELO-CMVEGFP were amplified by RCA as described in the example above. The amplification products were then purified using standard protocols of DNA purification.

The amplification products (DNA concatemers) were then treated with a protelomerase (TelN) following manufacturer's protocol, in particular with the following conditions:

Reaction volume: 1008 ul
DNA input: 350 μg amplified DNA
TelN input: 125 μl (625 units)
Reaction time: 30 min at 30° C., then 5min at 75° C.

Finally, the products from the reaction with TelN were digested with restriction enzymes and treated with exonuclease to remove the unwanted DNA fragments resulting from the protelomerase reaction.

HindIII and EcoRI digestion was performed following manufacturer's instructions. In brief:

Reaction volume: 1453 μl
DNA input: 350 μg of amplified DNA digested in TelN
EcoRI input: 150 μl (1500 units)
HindIII input: 150 μl (1500 units)
Reaction time: 60 min at 37° C., 15 min at 65° C.

Exonuclease III digestion was performed following manufacturer's instructions. In brief:

Reaction volume: 1628 μl
DNA input: 350 μg amplified DNA digested with TelN, HindIII and EcoRI
ExoIII input: 6 μl (600 units)
Reaction time: 45 min at 37° C. and 20 min at 80° C.

Figure 3:
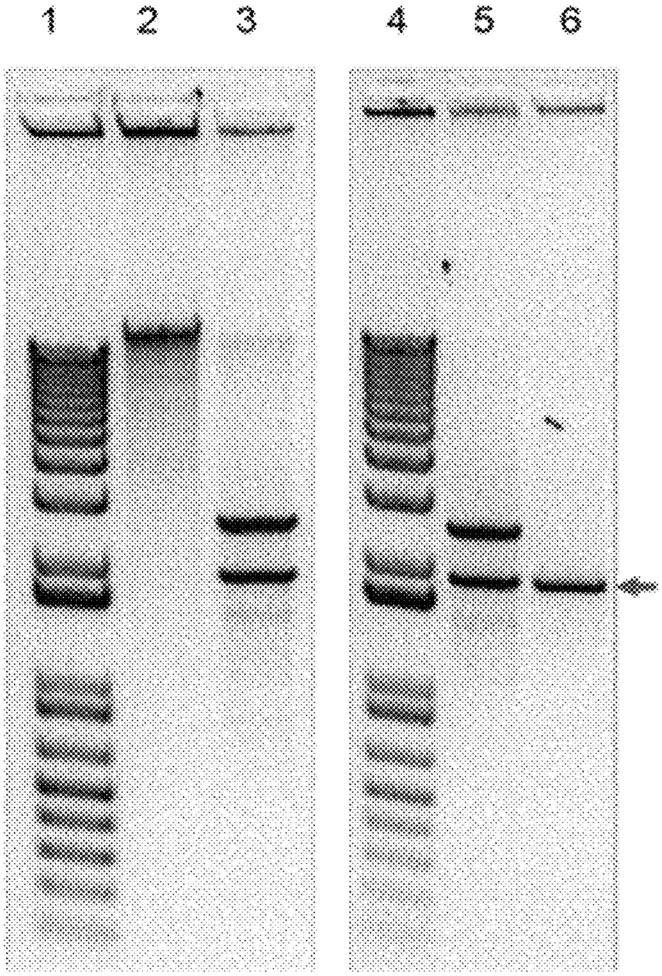
FIG. 3, related to Example 2, shows a picture of an agarose gel loaded with various product reactions: 1) DNA ladder; 2) TthPrimPol primed amplification of pUC57-Kan_TELO-CMV-EGFP; 3) TthPrimPol primed amplification of pUC57-Kan_TELO-CMV-EGFP digested with TelN; 4) DNA ladder; 5) TthPrimPol primed amplification of pUC57-Kan_TELO-CMV-EGFP digested with TelN, EcoRI and HindIII; 6) TthPrimPol primed amplification of pUC57-Kan_TELO-CMV-EGFP digested with TelN, EcoRI, HindIII and ExoIII. The arrow indicates the band size corresponding to the cassette (target molecule).

As shown in FIG. 3, the amplification primed TthPrimPol generated amplification products that could be successfully converted into clDNA by the action of TelN.

Finally, the resulting DNA was purified following standard procedures and giving a purification yield of 80.5 μg (760 µl at 106 ng/µl). The quality of the resulting clDNA products was analyzed by Sanger sequencing.

Example 3: clDNA Production from TelN-Generated clDNA Template

In order to test if TthPrimPol was capable of priming clDNAs with minimal single stranded loops that do not contain its target sequence "XTC", the plasmid pUC57-Kan_TELO-CMVEGFP, which contains two protelomerase recognition sequences flanking an expression cassette, was treated with a protelomerase (TelN) as described in Example 2, to generate clDNAs comprising the expression cassette.

1 ng of the resulting clDNAs or the initial plasmid were subjected to RCA amplification primed either with TthPrimPol or with random primers, as described in Example 1, and the amplification products were quantified. As shown in FIG. 4A, TthPrimPol priming allowed the amplification of TelN-generated clDNAs, although at lower yields than the amplification with random primers.

Then, the amplification products (DNA concatemers) were treated with TelN to generate once again clDNAs, and those were analyzed in an agarose gel by restriction enzyme and exonuclease treatment as described in Example 2.

Although random primer amplification produced a higher yield of DNA products (FIG. 4A), the analysis of the clDNA produced by TelN from the amplified DNA showed that TthPrimPol priming allowed producing higher levels of clDNAs containing the target DNA sequence (FIG. 4B).

These results demonstrate that TthPrimPol is not only capable of priming clDNA that contain minimal adaptor sequences (i.e. which do not contain its recognition sequence), but, more importantly, it is also able to generate amplification products of higher quality than random primers, which increase the production efficiency of the final clDNAs.

Example 4: Functional Validation of clDNAs Produced in the Process of the Invention clDNAs produced as disclosed above in Example 3 and containing a coding sequence for eGFP (enhanced green fluorescence protein), a plasmid vector containing a coding sequence for eGFP, an empty vector were transiently transfected into HEK293 cells as described in Heinrich, M. et al. "Linear closed mini DNA generated by the prokaryotic cleaving-joining enzyme TelN is functional in mammalian cells", J Mol Med, 2002, vol. 80, pp. 648-654.

Cells were analyzed at 24 h and 48 h by microscopy to measure the fluorescence intensity of cells following standard microcopy protocols.

Figure 4:
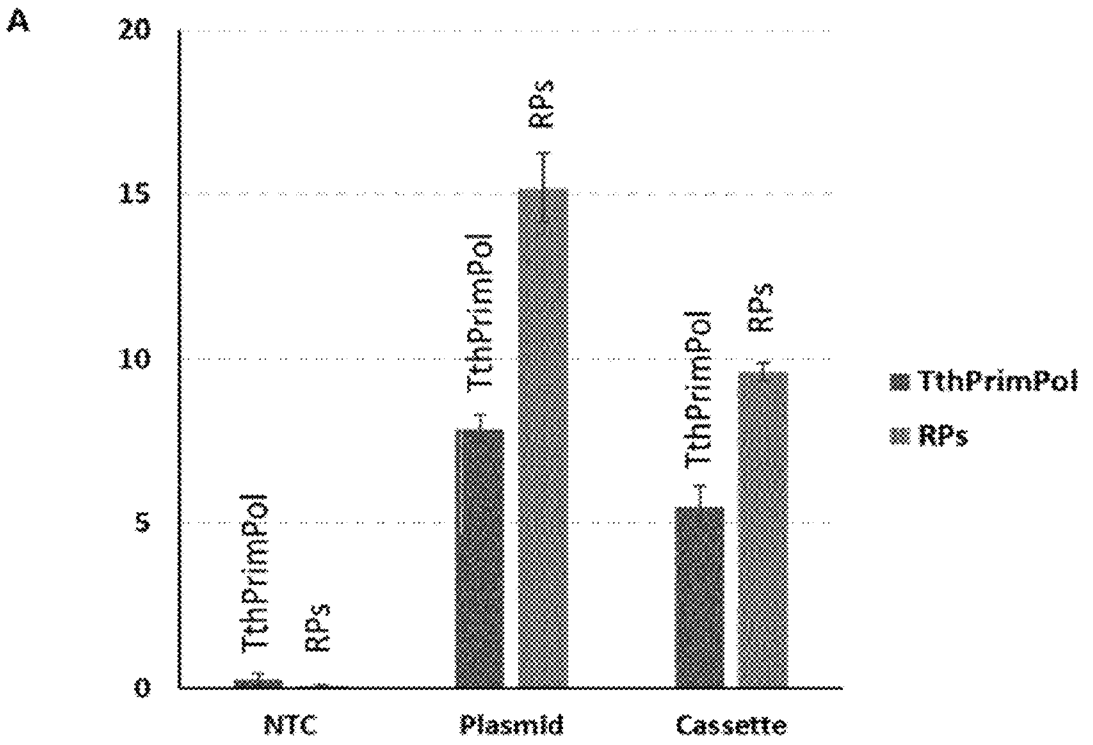
FIG. 4, related to Example 3, shows the RCA amplification clDNA generated with TelN. A) DNA yield resulting from the RCA amplification of a plasmid template or a clDNA template generated by TelN, where the amplification is primed either by TthPrimPol or random primers (RPs). The y-axis represents the DNA yield in µg. NTC refers to the control reaction, without template DNA. B) Picture of agarose gel loaded with the DNA amplification products obtained with the conditions indicated and treated or not with TelN. Before loading, the DNA products were treated with EcoRI, HindIII and ExoIII. The arrow indicates the band size corresponding to the cassette (target molecule).
Figure 4:
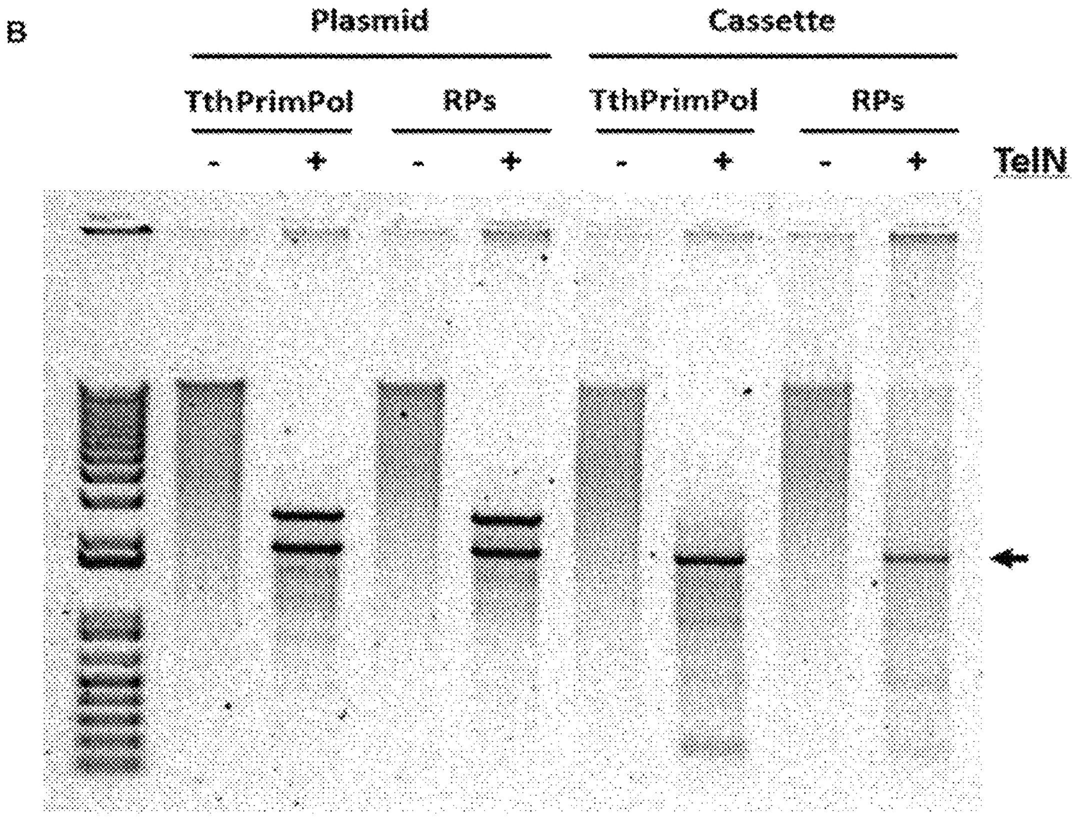
Figure 5:
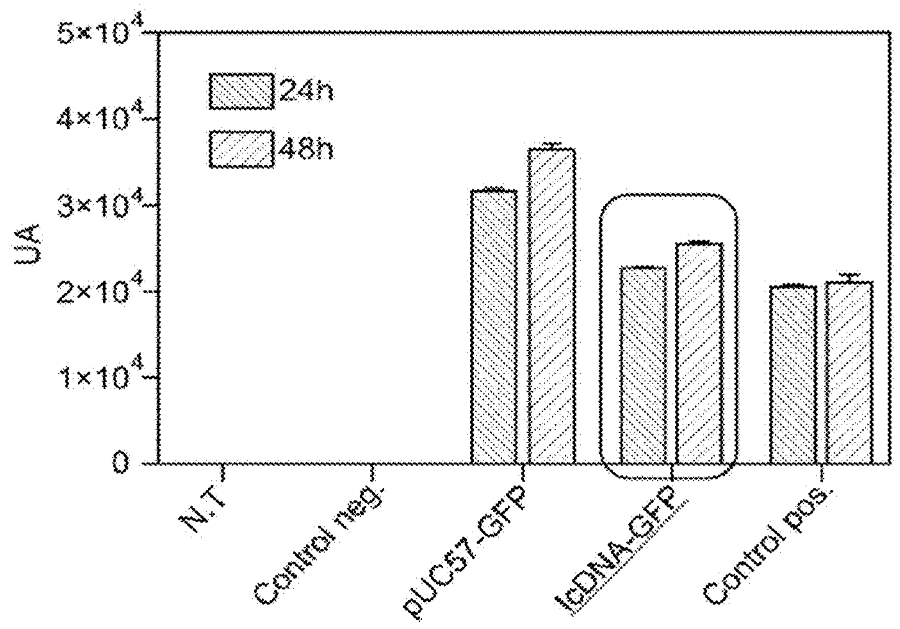
FIG. 5, related to Example 4, shows a quantification of the fluorescence intensity of HEK293 cells 24 h and 48 h after transfection with the constructs indicated. N.T. means not treated cells. The y-axis represents Arbitrary units of fluorescence intensity.
Figure 6:
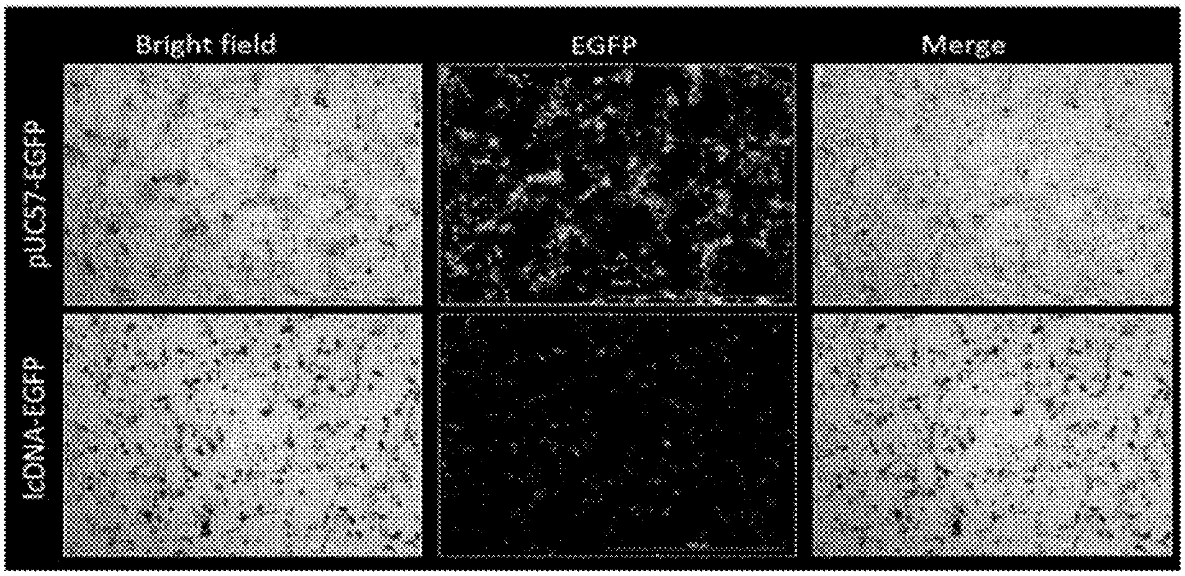
FIG. 6, related to Example 4, shows representative images of HEK293 cells 24 h and 48 h after transfection with the constructs indicated.

As shown in FIGS. 4 and 5, cells transfected with the clDNAs synthesized following the process of the invention presented a strong expression of eGFP. These results demonstrate that the process of the invention allows the production of highly functional clDNAs suitable for gene therapy.

Example 5: clDNA Production Containing Customized Single Stranded DNA Adaptors from TelN-Generated clDNA Template via RCA Synthesis of Customized Single Stranded DNA Adaptors Containing Natural and Modified Nucleotides Customized single stranded DNA adaptors containing natural and modified nucleotides were synthesized following standard phosphoramidite chemistry (Beaucage S. L. et al, 1981) including at least two of the following modified nucleotides: 8-oxo-deoxyadenosine (8-oxo-dA), 5-Fluoro-deoxyuracil (5FU), inosine, thiophosphate nucleotide, or locked nucleic acid (LNA) nucleotide.

Briefly, Phophoramidite synthesis begins with the 3'-most nucleotide and proceeds through a series of cycles composed of fours steps that are repeated until the 5'-most nucleotide is attached. These steps are deprotection(i), coupling(ii), oxidation(iii), and capping(iv).

This cycle is repeated for each nucleotide in the sequence. At the end of the synthesis the oligonucleotide exists as, for example, a 25-mer with the 3' end still attached to the CPG and the 5' end protected with a trityl group. In addition, protecting groups remain on three of the four bases to maintain the integrity of the ring structures of the bases. The protecting groups are benzoyl on A and C and N-2-isobutyryl on G. Thymidine needs no protecting group. The completed synthesis is detritylated and then cleaved off the controlled pore glass leaving a hydroxyl on both the 3' and 5' ends. At this point the oligo (base and phosphate) is deprotected by base hydrolysis using ammonium hydroxide at high temperature. The final product is a functional single-stranded DNA molecule.

Corresponding hairpin DNA adaptors containing natural oligonucleotides were also synthesized. The list of synthesized adaptors is provided in table 2.

Upon synthesis completion, the oligonucleotides were cleaved from the support and the protecting groups removed. standard purification step (e.g. PAGE, HPLC and/or RNase Free HPLC) was then employed to separate the full-length product from the truncated sequences.

TABLE 2 single stranded DNA adaptors containing natural and modified nucleotides

| Sample Name | Oligo sequence | SEQ ID |
|---|---|---|
| Oligo 15 | AGGGATCCACTCAGGAT | SEQ ID NO: 10 |
| Oligo 37 | AGGGATCC*A*C*T*C*AGGAT | SEQ ID NO: 11 |
| Oligo 4 | AGGGCTAACCACTCAGGTTAG | SEQ ID NO: 12 |
| Oligo 28 | AGGGCTAACC/i8-oxo-dA/CTC/i8-oxo-dA/GGTTAG | SEQ ID NO: 13 |
| Oligo 29 | AGGGCTAACCA/i5F-dU/T/i5FdU/AGGTTAG | SEQ ID NO: 14 |
| Oligo 17 | AGGGATAACATGGCCACTCAGGCCATGTTAT | SEQ ID NO: 15 |

TABLE 2-continued

| single stranded DNA adaptors containing natural and modified nucleotides | | |
|---|---|---|
| Sample Name | Oligo sequence | SEQ ID |
| Oligo 19 | AGGGATAACA+T+G+G+C+CACTCAGGCCATGTTAT | SEQ ID NO: 16 |
| Oligo 22 | AGGGATAACATGGCC/i8-oxo-dA/CTC/i8-oxo-dA/GGCCATGTTAT | SEQ ID NO: 17 |
| Oligo 21 | AGGGATAACATGGCC/I/CTC/I/GGCCATGTTAT | SEQ ID NO: 18 |
| Oligo 41 | AGGGCTTACG*C*G*C*GTAAG | SEQ ID NO: 19 |

*phosphothioated nucleotide to the right (eg Oligo 37, phosphothioated nucleotides are: ACTCA)+, LNA nucleotide to the right (eg Oligo 19, LNA nucleotides are: TGGCC)
/I/ inosine nucleotide
i8-oxo-dA, 8-oxo-deoxyadenosine nucleotide
i5F-dU, 5-Fluoro-deoxyuracil nucleotide

Figure 9:
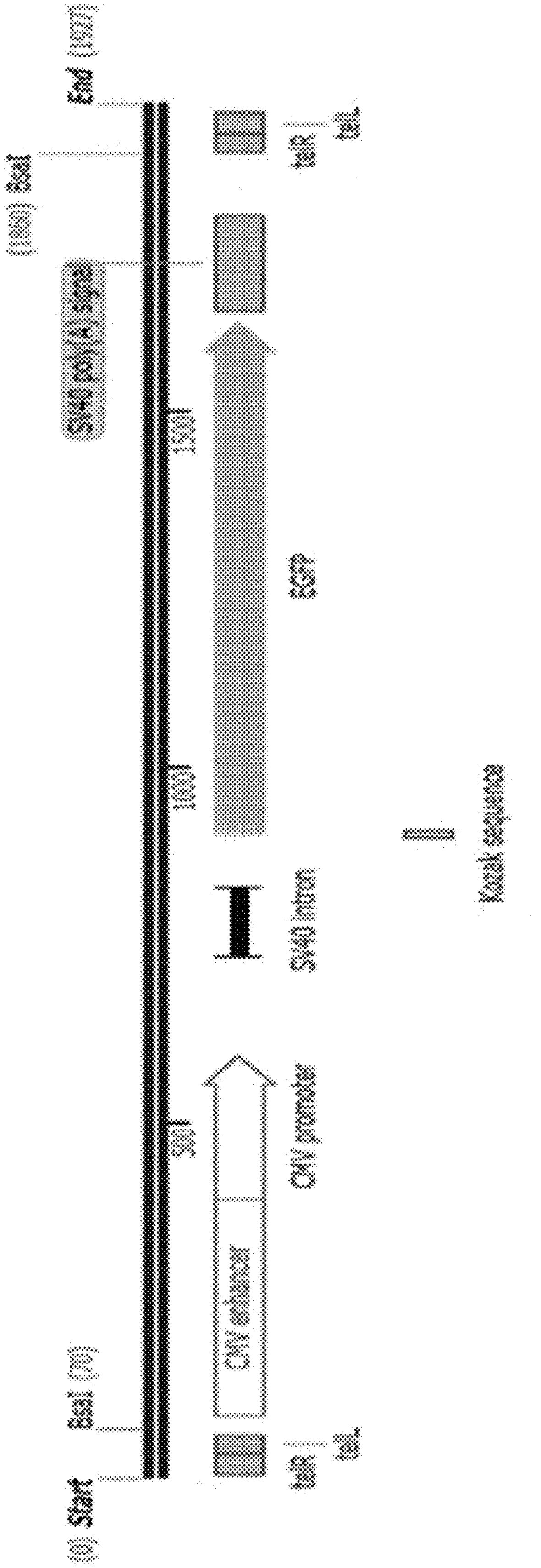
FIG. 9 shows representation of a fragment of eGFP plasmid (the plasmid having SEQ ID NO: 20) containing the sequence of interest for preparation of clDNA of the invention. The represented fragment comprises the sequence of interest (in this case the sequence encoding for GFP) together with additional sequences such as corresponding promoter and enhancer. The sequence of interest is flanked by BsaI restriction sites and protelomerase target sequences

Preparing clDNA with Customized Adaptors from Plasmidic DNA clDNAs were prepared using some of the customized adaptors of table 2 and starting from a plasmid DNA (pDNA). First, the pDNA, for example the eGFP plasmid having SEQ ID NO: 20 (which comprises the sequence of interest encoding for Gfp flanked by BsaI restriction sites, as well as protelomerase target sequences (see FIG. 9), was treated with protelomerase to yield clDNA comprising the sequence of interest flanked by endonuclease restriction sites. Then this clDNA was amplified via rolling circle amplification (RCA) using TthPrimPol and Phi29. The resulting concatamers were purified and treated with the corresponding restriction enzyme (eg BsaI) and ligated with customized adaptors; for example, with oligos 21 and 41 from table 2. An exemplary detailed protocol is provided below.

A. Protocol for Obtaining clDNA from Plasmid DNA

TABLE 4

| Summary of experimental instruments | | |
|---|---|---|
| Instrument | Brand/manufacturer | Model |
| Balance | Mettler Toledo | ME4002E |
| pH meter | INSEA | PHSJ-5 |
| Centrifuge | ThermoFisher | Heraeus ™ Pico ™ 21 |
| Clean bench | AIRTECH | SW-CJ-2FD |

TABLE 5

| Summary of material information | | | |
|---|---|---|---|
| No. | Material name | Brand or Manufacturer | Cat. No. |
| 1 | Exonuclease III | NEB | M0206 |
| 2 | NEBuffer 1 | NEB | M0206 |
| 3 | TritonX-114 | Solarbio | T8210 |
| 4 | Isopropyl alcohol | Sinopharm Chemical Reagent Co., Ltd. | 67-63-0 |
| 5 | KpnI | NEB | R3142L |
| 6 | HindIII | NEB | R3104S |
| 7 | CutSmart buffer | NEB | B7204S |
| 8 | TelN | GenScript | NA |
| 9 | TelN buffer | GenScript | NA |

1.1 TelN Digestion

The eGFP plasmid was digested by TelN enzyme at 30° C. for 2 h and inactivated at 75° C. for 10 min. Scaling up accordingly when performing several reactions at the same time.

TABLE 6

| TelN enzyme digestion reaction | |
|---|---|
| COMPONENTS | 20 mL of REACTION |
| 10X Buffer | 2 mL |
| Plasmid | 10 mg, 10 mL |
| TelN | Actual addition: $1.0 \times 10^6$ U(2 mL, 50 U/µL) |
| Sterile water | Add to 20 mL |

1.2 Backbone Removal

1.2.1 Kpn I and Hind III Digestion

The product from last step was digested with Kpn I and Hind III at 37° C. for 1 h. Then, the sample was inactivated at 65° C. for 15 minutes. Scaling up accordingly when performing several reactions at the same time.

TABLE 7

| Kpn I and Hind III digestion reaction | |
|---|---|
| COMPONENTS | 25 mL of REACTION |
| 10x Cutsmart | 2.5 mL |
| Plasmid from last step | 20 ml |
| Kpn I | Actual addition: 10000 U (500 µL, 20 U/µL) |
| Hind III | Actual addition: 10000 U (500 µL, 20 U/µL) |
| Sterile water | Add to 25 mL |

1.2.2 Exo III Digestion

Exo III digestion at 37° C. for 1 h and inactivated at 75° C. for 10 min. Scaling up accordingly when performing several reactions at the same time.

TABLE 8

| Exo III digestion reaction | |
|---|---|
| COMPONENTS | 28 mL of REACTION |
| 10x NEBuffer 1 | 2.8 mL |
| Plasmid from last step | 25 mL |
| Exo III | Actual addition: 30000 U( 300 µL, 100 U/µL) |

1.3 Purify clDNA with Gel Filtration Chromatography and Isopropanol

1.3.1 Gel Filtration Chromatography

Buffer A: 10 mM Tris-HCl, pH 7.5
Column: Bestarose 6 FF 153 mL
Sample: 28 ml
Flow: 60 cm/h
Collect fraction: 20 mAU-20 mAU, 40 mL
CIP: 1 M NaOH+pure water
Storage: pure water

1.3.2 Endotoxin Removing and Isopropanol Precipitation

Add 3 M sodium acetate and 15% Triton-114 to the sample from last step and mix by vortexing shown as table 6. Keep the sample at 4° C. for 5 min. Then, centrifuge at 12000 g for 20 min at 25° C. After centrifugation, collect supernatant and add the equal volume of isopropanol to the supernatant and mix completely. Keep the sample at room temperature for 5 min. After that, centrifuge at 12000 g for 20min and remove the supernatant. Finally, suspend the precipitate with 10 mM Tris-HCl (pH 7.5).

TABLE 9

| Triton-114 system | |
|---|---|
| Material | Addition amount (A is the volume of clDNA) |
| clDNA | A(40 mL, ~100 µg/mL) |
| 15% Triton 114 | 0.1 A (4 mL) |

After three steps of enzyme digestion, gel chromatography, Triton 114 treatment and isopropanol precipitation, the eGFP_BsaI_clDNA was made successfully. The DNA homogeneity (%) of the sample according to HPLC chromatogram was 97%. Endotoxin of the sample <10 EU/mg.

B. Protocol for Obtaining clDNA Containing Customized Adaptors from clDNA via RCA This experiment is designed to produce clDNA containing customized adaptors from the eGFP_BSaI_clDNA obtained in the section above by Trueprime-RCA Kit.

TABLE 10

| Summary of experimental instruments | | |
|---|---|---|
| Instrument | Brand/manufacturer | Model |
| Balance | Mettler Toledo | ME4002E |
| pH meter | INSEA | PHSJ-5 |
| Centrifuge | ThermoFisher | Heraeus ™ Pico ™ 21 |
| Clean bench | AIRTECH | SW-CJ-2FD |

TABLE 11

| Summary of material information | | | |
|---|---|---|---|
| No. | Material name | Brand or Manufacturer | Cat. No. |
| 1 | Exonuclease III | NEB | M0206 |
| 2 | NEBuffer 1 | NEB | M0206 |
| 3 | TritonX-114 | Solarbio | T8210 |
| 4 | Isopropyl alcohol | Sinopharm Chemical Reagent Co., Ltd. | 67-63-0 |
| 5 | Kpnl | NEB | R3142L |
| 6 | Hindlll | NEB | R3104S |
| 7 | CutSmart buffer | NEB | B7204S |
| 8 | 4BBTM TruePrime ® RCA kit | 4basebio | 390100 |
| 9 | Buffer D | 4basebio | 390100 |
| 10 | Buffer N | 4basebio | 390100 |
| 11 | Reaction Buffer | 4basebio | 390100 |
| 12 | Enzyme 1 (TthPrimPol) | 4basebio | 390100 |
| 13 | Enzyme 2 (Phi29 DNA polymerase) | 4basebio | 390100 |
| 14 | TeIN | GenScript | NA |
| 15 | TeIN buffer | GenScript | NA |
| 16 | AxyPrep DNA Gel Extraction Kit | Axygen | AP-GX-250 |
| 17 | Buffer DE-B | Axygen | AP-GX-250 |
| 18 | Buffer W1 | Axygen | AP-GX-250 |
| 19 | Buffer W2 | Axygen | AP-GX-250 |
| 20 | T4 ligase | NEB | M0202T |
| 21 | T4 ligase buffer | NEB | M0202T |
| 22 | Bsal | NEB | R3733L |
| 23 | T4 PNK | NEB | M0201L |
| 24 | T4 PNK buffer | NEB | M0201L |

1.1 RCA

✧ Always mix by pipetting. DO NOT VORTEX

✧ Transfer 10 µl of clDNA (≥1 ng/µl) into a clean tube

✧ Add 10 µl of Buffer D and incubate at room temperature for 3 minutes

✧ Neutralize the reaction by adding 10 µl of Buffer N to each tube

✧ Keep the samples at room temperature until use*

✧ Prepare the amplification mix adding the components in the order listed in the following table ✧ Incubate at 30° C. for 3 hours**. Inactivate the reaction at 65° C. for 10 minutes.

✧ Cool down to 4° C. Store amplified DNA at 4° C. for short-term storage or −20° C. for long-term storage.

(*) It is highly recommended to perform the amplification reaction just after the sample has been denatured.

(**) Incubation time can be increased up to 6 hours if higher amplification yields are required.

Scaling up accordingly when performing several reactions at the same time.

TABLE 12

| RCA-100 ul system | | |
|---|---|---|
| Material | Add amount | Comments |
| clDNA | 10 uL | (>1 μg/mL, total 80 ng) |
| Buffer D | 10 uL | 3 min at RT |
| Buffer N | 10 uL | Neutralization |
| $H_2O$ | 37.2 μL | Amplification mix |
| Reaction buffer | 10 uL | |
| dNTPs | 10 uL | |
| Enzyme 1 (TthPrimPol) | 10 uL | |
| Enzyme 2 (Phi29 DNA polymerase) | 2.8 uL | |

1.2 Purify RCA Product (Concatamers) with Isopropanol (as Described Above)

1.3 Purify RCA Product (Concatamers) with Axygen Kits. (Optional)

If the sample is no more than 100 uL, Axygen kit could also be used to purify clDNA. The protocol is described below and bottles containing buffers labeles as described:.

1) Add 2× sample volume of Buffer DE-B, mix.

2) Place a Miniprep column into a 2 ml microfuge tube. Transfer the sample from last step into the column. Centrifuge at 12,000 xg for 1 minute.

3) Discard the filtrate from the 2 ml microfuge tube. Return the Miniprep column to the 2 ml microfuge tube and add 500 μl of Buffer W1. Centrifuge at 12,000 xg for 30 seconds.

4) Discard the filtrate from the 2 ml microfuge tube. Return the Miniprep column to the 2 ml microfuge tube and add 700 μl of Buffer W2. Centrifuge at 12,000 xg for 30 seconds 5) Discard the filtrate from the 2 ml microfuge tube. Place the Miniprep column back into the 2 ml microfuge tube. Add a second 700 μl aliquot of Buffer W2 and centrifuge at 12,000 xg for 1 minute 6) Transfer the Miniprep column into a clean 1.5 ml microfuge tube (provided). To elute the DNA, add 50 μl of 10 mM Tris-HCL (pH 7.5) to the center of the membrane. Let it stand for 1 minute at room temperature. Centrifuge at 12,000 xg for 1 minute.

1.4 Oligo Denaturation and Annealing

Oligo (e.g. from table 3: oligo 21 or oligo 41) was denatured at 95° C. for 10 min and annealed naturally at room temperature for 30 min. Scaling up accordingly when performing several reactions at the same time.

TABLE 13

| Oligo denaturation and annealing | |
|---|---|
| Material | Add amount |
| Phosphorylated Oligo | 95 μL |
| 20X SSC | 5 μL |

1.5 Oligo Phosphorylation (Optional, Skip this Step if the Oligo is already Phosphorylated)

Oligo phosphorylation at 37° C. for 1 h.

TABLE 14

| Oligo phosphorylation | |
|---|---|
| Material | Add amount |
| Oligo without phosphorylation | 80 μL |
| T4 PNK buffer | 10 μL |
| T4 PNK | 10 μL |

1.6 BsaI Digestion

BsaI digestion at 37° C. for 2h and inactivated at 75° C. for 10 min.

TABLE 15

| 100 uL digestion system of BsaI | |
|---|---|
| Material | Add amount |
| purified RCA product | 85 μL |
| CutSmart buffer | 10 μL |
| BsaI | 20 U/μL, 1 μL |
| Sterile water | Add to 0.1 mL |

1.7 Purify BsaI-digested RCA Product with Isopropanol (as Described Above)

1.8 Purify BsaI-digested RCA Product with Axygen kits. (Optional the Sample is No More Than 100 uL; as Described Above)

1.9 T4 Ligation

T4 ligation at 16° C. overnight and inactivated at 75° C. for 10 min.

TABLE 16

| 100 uL T4 ligation system | |
|---|---|
| Material | Add amount |
| Oligo | 5 uL (~1 μg/μL) |
| BsaI-digested clDNA | 85 uL (~100 ng/uL) |
| T4 ligase buffer | 10 μL |
| T4 ligase | 20000U, 1 μL |
| Sterile water | Add to 0.1 mL |

1.10 Advanced Golden Gate Assembly (Optional)

Conventional ligation methods usually require several cloning steps to generate a construct of interest. At each step, a single DNA fragment is transferred from a donor plasmid or PCR product to a recipient vector.

While Golden Gate cloning, allows assembling up to fifteen fragments at a time in a recipient plasmid. Cloning is performed by pipetting in a single tube all plasmid donors, the recipient vector, a type IIS restriction enzyme and ligase, and incubating the mix in a thermal cycler. So we would also suggest to make oDNA with Golden Gate Assembly. The system and condition were described as table 14 and 15, respectively. Scaling up accordingly when performing several reactions at the same time

TABLE 17

Advanced Golden Gate Assembly system

| Material | Add amount |
| --- | --- |
| 10X T4 ligase buffer | 10 μL |
| clDNA(amplified by RCA) | 24 μg |
| Oligo | 72 μg |
| Bsal | (100U) 5 uL |
| T4 DNA ligase | (20000U) 1 uL |
| Nuclease-free water | up to 200 μL |

TABLE 18

Advanced Golden Gate Assembly condition

| Temperature | Time | |
| --- | --- | --- |
| 37° C. | 3 min | 25 cycles |
| 22° C.* | 5 min | |
| 22° C. | 60 min | |
| 50° C. | 5 min | |
| 80° C. | 10 min | |
| 4° C. | Store the sample at 4° C. until use | |

*The optimal temperature of T4 ligase from NEB is 16° C. and 22° C. for T4 ligase from Thermofisher.

1.11 Digestion of Unexpected DNA

Exo III digestion at 37° C. for 1 h and inactivated at 75° C. for 10 min. Scaling up accordingly when performing several reactions at the same time.

TABLE 19

Exo III digestion reaction

| COMPONENTS | 0.3 mL of REACTION |
| --- | --- |
| 10x NEBuffer 1 | 30 μL |
| Plasmid from last step | 0.2 mL |
| Exo III | 200 U(2 μL, 100U/μL) |
| Nuclease-free water | up to 300 μL |

1.12 Purify oDNA with Isopropanol (Described Above)

1.13 Purify oDNA with Axygen kits. (Optional the Sample is No More Than 100 uL; as Described Above)

The eGFP_BsaI_oDNA was successfully made with oligos 21 and 41:

TABLE 20

| Sample | Conc. (ng/μL) | Volume (ml) | Total (μg) | Homogeneity (%) |
| --- | --- | --- | --- | --- |
| oDNA21 | 119.6 | 0.05 | 6.0 | 95.6 |
| oDNA41 | 130.0 | 0.05 | 6.5 | 96.2 |

Figure 10:
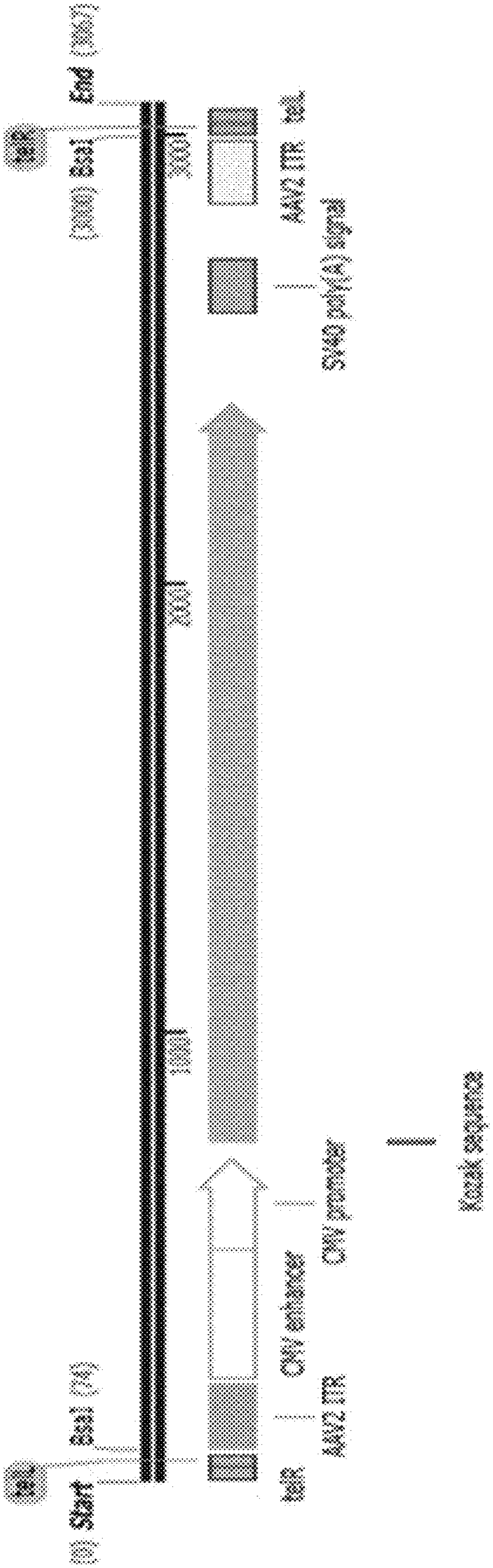
FIG. 10 shows representation of a fragment of Luc-ITR (the plasmid having SEQ ID NO: 22) containing the sequence of interest for preparation of clDNA of the invention. The represented fragment comprises the sequence of interest (in this case the sequence encoding for Luciferase) together with additional sequences such as corresponding promoter and enhancer, as well as AVV2-ITRs. The sequence of interest is flanked by BsaI restriction sites and protelomerase target sequences.
Figure 11:
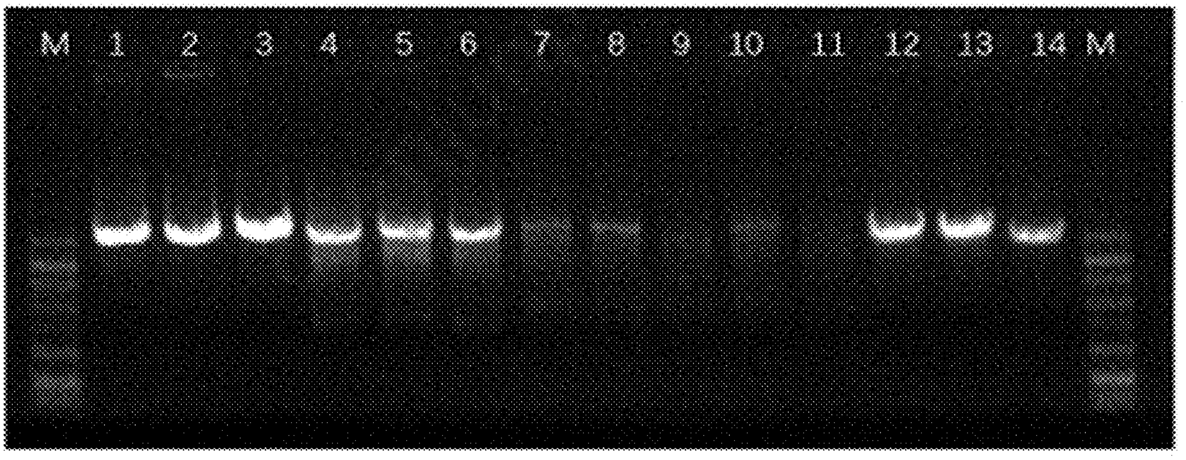
FIG. 11 shows Agarose gel electrophoresis of oDNA $4_{ITR}$ (M, DL3000 ladder; Lane 12, oDNA $4_{ITR}$).

The same procedure was used to prepare clDNAs starting from Luc plasmid having SEQ ID NO: 21 (which comprises the sequence encoding for luciferase flanked by BsaI restriction sites, as well as protelomerase target sequences) and oligos 15, 37, 4, 28, 29, 17, 22. 37, 28, 29, 19 and 22 from table 2. The same procedure was also used to prepare clDNAs starting from Luc-ITR plasmid having SEQ ID NO: 22 (wherein the sequence of interest additionally comprises ITRs flanking the sequence encoding for luciferase which is flanked by BsaI restriction enzyme as well as protelomerase target sequences, see FIG. 10) and oligo 4; thus, leading to oDNA $4_{ITR}$ (6.2 μg in total)—FIG. 11 (agarose gel electrophoresis)

Figure 7:
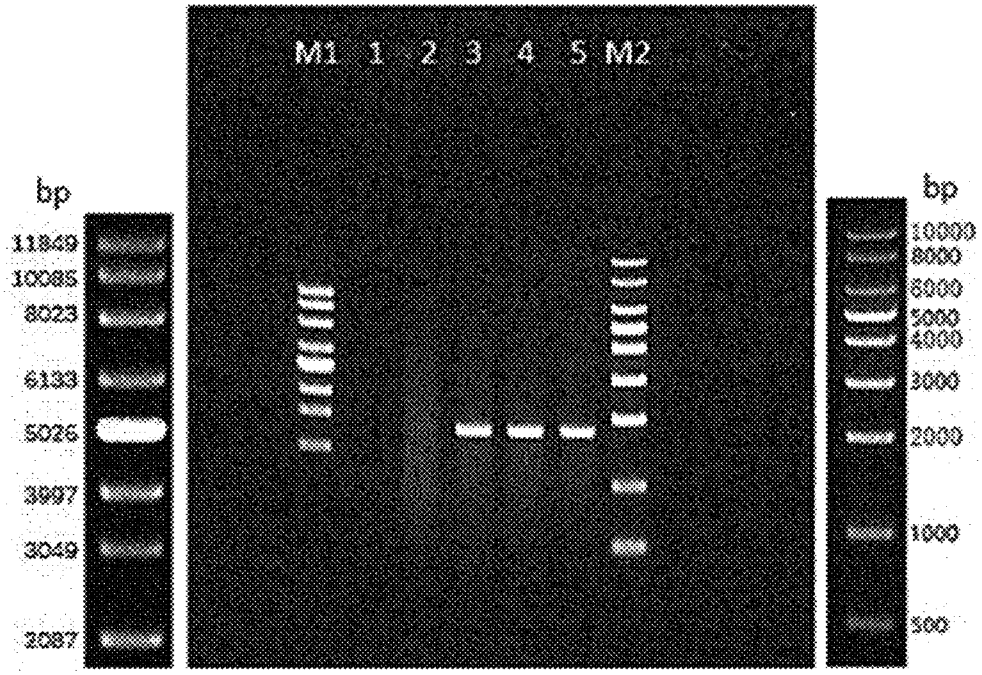
FIG. 7 shows quality control parameters for oDNA 41. A, Agarose gel electrophoresis (M1, supercoiled DNA Ladder Marker TAKARA: 3585A; M2, 1 kb DNA Ladder TIAGEN MD111; lane 5, oDNA 41); B, Grayscale analysis; D, Sanger Sequencing.
Figure 7:
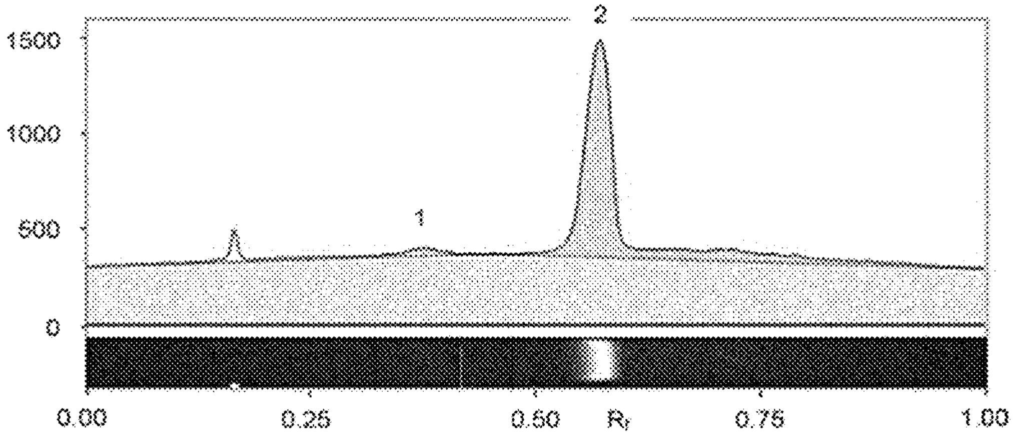
Figure 7:
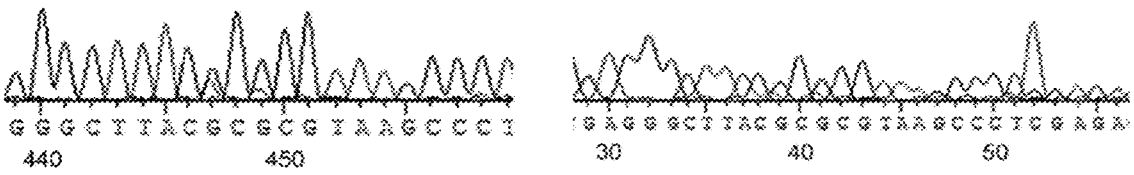
Figure 8:
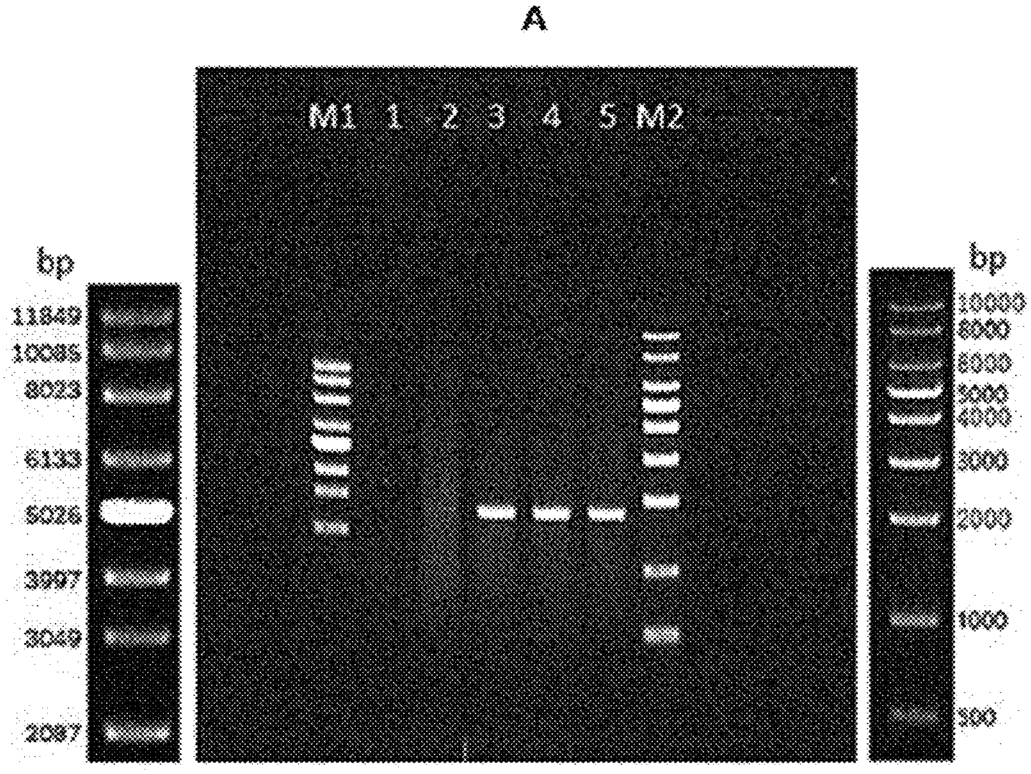
FIG. 8 shows quality control parameters for oDNA 21. A, Agarose gel electrophoresis (M1, supercoiled DNA Ladder Marker TAKARA: 3585A; M2, 1 kb DNA Ladder TIAGEN MD111; lane 4, oDNA 21); B, Grayscale analysis; D, Sanger Sequencing.
Figure 8:
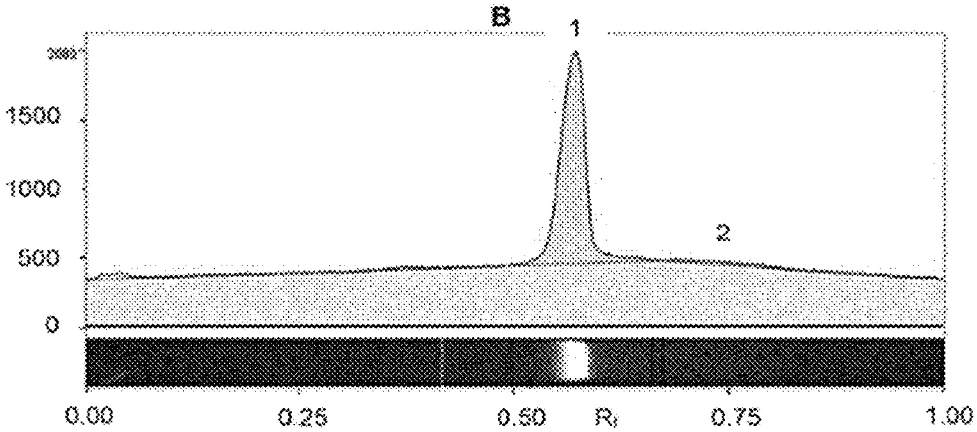
Figure 8:
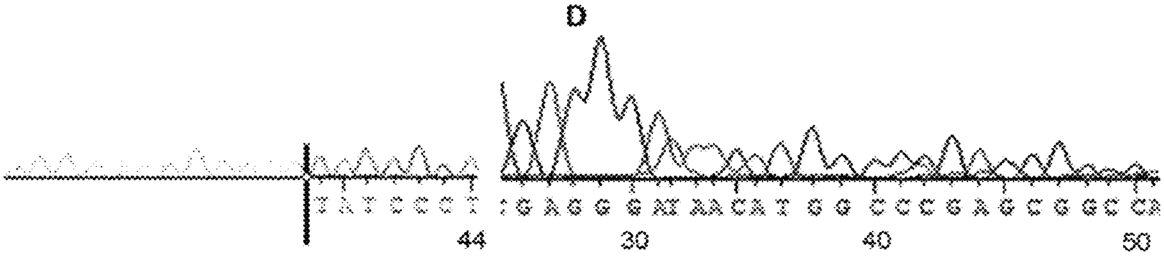

The quality of the obtained clDNA was determined by standard procedures, in particular, Agarose gel electrophoresis, Grayscale analysis, anion-exchange chromatography-HPLC and Sanger Sequencing. It was found that all clDNAs showed good quality features in terms of purity, peak resolution and sequence confirmation. For illustration, results for oDNA41 and oDNA21 are shown in FIGS. 7 and 8, respectively.

Example 6. clDNA Production from TelN-Generated clDNA Template via RCA Followed by TelN Processing Alternatively, the clDNA of the invention may be prepared by the procedure described in example 5 from section A, 1.1, to section B, 1.3, followed by TelN processing of the resulting concatemers. This last step, processing of the concatemers obtained from RCA (section B, 1.3) with protelomerase, is described in detail below.

1.4 TelN Digestion

The purified RCA product was digested by TelN enzyme at 30° C. for 2 h and inactivated at 75° C. for 10 min. Scaling up accordingly when performing several reactions at the same time

TABLE 21

TelN enzyme digestion reaction

| COMPONENTS | 0.5 mL of REACTION |
| --- | --- |
| 10X TelN Buffer | 0.05 mL |
| Purified RCA product (concatamers) | 80 μg, 0.3 mL |
| TelN | 1500 U(0.03 mL, 50 U/μL) |
| Sterile water | Add to 0.5 mL |

1.5 Backbone Removal

1.4.1 Kpn I and Hind III Digestion

The product from last step was digested with Kpn I and Hind III at 37° C. for 1 h. Then, the sample was inactivated at 65° C. for 15 minutes. Scaling up accordingly when performing several reactions at the same time.

TABLE 22

Kpn I and Hind III digestion reaction

| COMPONENTS | 0.6 mL of REACTION |
| --- | --- |
| 10x Cutsmart | 60 μL |
| clDNA from last step | 0.5 mL |

TABLE 22-continued

| Kpn I and Hind III digestion reaction | |
|---|---|
| COMPONENTS | 0.6 mL of REACTION |
| Kpn l | Actual addition: 400 U (20 μL, 20 U/μL) |
| Hind I | Actual addition: 400 U (20 μL, 20 U/μL) |

1.4.2 Exo III Digestion

Exo III digestion at 37° C. for 1 h and inactivated at 75° C. for 10 min. Scaling up accordingly when performing several reactions at the same time.

TABLE 23

| Exo III digestion reaction | |
|---|---|
| COMPONENTS | 0.67 mL of REACTION |
| 10x NEBuffer 1 | 62 μL |
| clDNA from last step | 0.6 mL |
| Exo III | 800 U(80 μL, 100U/μL) |

1.6 Purify clDNA with Isopropanol (as Described Above)

1.7 Purify clDNA Product with Axygen Kits. (Optional if the Sample is No More than 100 uL; as Defined Above)

Figure 12:
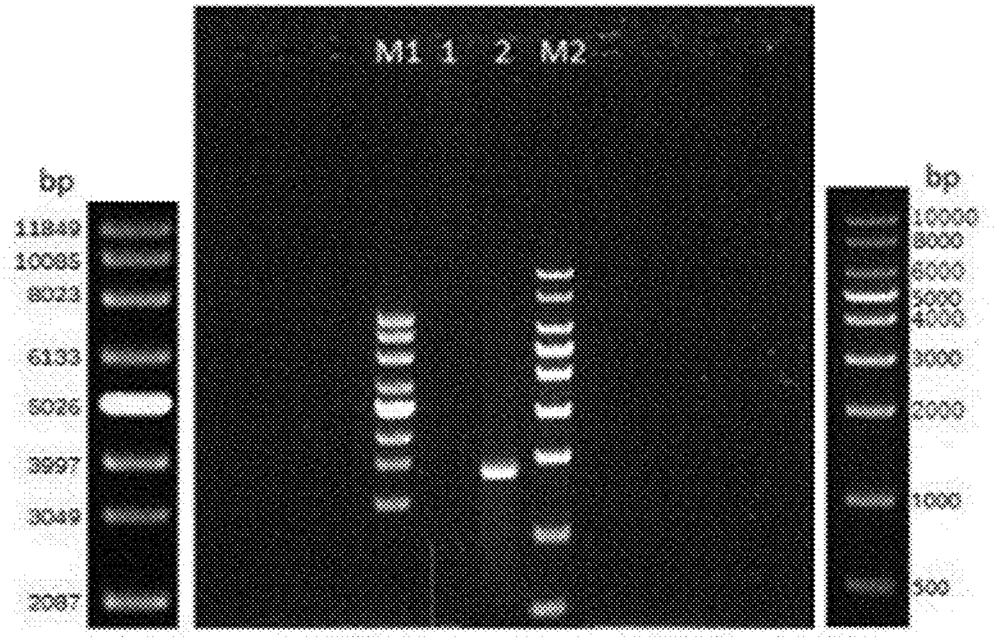
FIG. 12 shows Agarose gel electrophoresis of clDNA obtained from eGFP plasmid (the plasmid having SEQ ID NO: 20) as in example 6 (RCA followed by protelomerase treatment) (M1, supercoiled DNA Ladder Marker TAKARA: 3585A; M2, 1 kb DNA Ladder TIAGEN MD111; lane 2, clDNA from example 6).

Synthesized clDNA, which sequence of interest encodes GFP (see FIG. 9), bear the constant 28 base pair protelomerase sequence obtained after cleavage/joining. Details about synthesis performance, step by step, are described in Table 24 (below); obtained clDNA showed 96.6% homogeneity according to the Agarose Gel Electrophoresis (AGE)—FIG. 12

TABLE 24

| Recovery of key steps as followed: | | | | |
|---|---|---|---|---|
| | Volume (μL) | Conc (μg/mL) | Total (μg) | Rec (%) |
| Template Plasmid | 300 | 15 | 4.5 | NA |
| Purified RCA product | 1500 | 260 | 390 | ~86 folds yield |
| Purified clDNA | 1200 | 121.6 | 145.9 | 37.41% |

Citation List

Heinrich, M. et al. “Linear closed mini DNA generated by the prokaryotic cleaving-joining enzyme TelN is functional in mammalian cells”, J Mol Med, 2002, vol. 80, pp. 648-654

Altschul et al., “Basic local alignment search tool”, 1990, J. Mol. Biol, vol. 215, pp. 403-410

Xiao X. et al., “A novel 165-base-pair terminal repeat sequence is the sole cis requirement for the adeno-associated virus life cycle”, 1997, J Virol., vol. 71(2), pp. 941-948.

WO2011000997

Beaucage S. L. et al, Deoxynucleoside phosphoramidites—A new class of key intermediates for deoxypolynucleotide synthesis. Tetrahedron Letters, Volume 22, Issue 20, 1981, Pages 1859-1862

The invention claimed is:

1. A process for the production of a closed linear DNA comprising the steps of:

a) providing a closed linear DNA template comprising a double-stranded middle segment comprising a DNA sequence of interest flanked by two single-stranded loops, wherein the single-stranded loops do not comprise a primase/polymerase priming site;

b) amplifying DNA from the closed linear DNA template of step (a) wherein the amplification is primed with a primase/polymerase enzyme of SEQ ID NO:1;

c) generating a closed linear DNA with the amplified DNA produced in step (b); and d) purifying the closed linear DNA produced in step (c).

2. The process according to claim 1, wherein the amplification performed in step (b) is a rolling-circle amplification.

3. The process according to claim 1, wherein the amplification of step (b) is carried out with a strand displacement DNA polymerase.

4. The process according to claim 1, wherein step (a) is performed by contacting a plasmid vector comprising at least two restriction sites flanking the DNA sequence of interest with at least one restriction enzyme thereby producing open double stranded DNA containing the DNA sequence of interest, and attaching single stranded DNA adaptors to both ends of the open double stranded DNA containing the DNA sequence of interest.

5. The process according to claim 1, wherein step (a) is performed by contacting a plasmid vector comprising at least two protelomerase target sequences flanking the DNA sequence of interest with a protelomerase.

6. The process according to claim 1, wherein the amplified DNA resulting from step (b) is a concatameric DNA comprising repeats of the DNA sequence of interest, wherein each one of the repeated DNA sequences of interest is flanked by restriction sites and/or protelomerase target sequences.

7. The process according to claim 6, wherein when the concatameric DNA comprises repeats of the DNA sequence of interest flanked by at least restriction sites, then step (c) is performed by:

(c.1) contacting the concatameric DNA with at least one restriction enzyme thereby producing a plurality of open double stranded DNA fragments each containing the DNA sequence of interest, and (c.2) attaching a single stranded DNA adaptor to each of both ends of the open double stranded DNA fragments.

8. The process according to claim 6, wherein when the concatameric DNA comprises repeats of the DNA sequence of interest flanked by at least a protelomerase target sequence, then step (c) is performed by contacting the concatameric DNA with a protelomerase.

9. The process according to claim 1, wherein step (a) is performed by contacting a plasmid vector comprising two protelomerase target sequences flanking at least two restriction sites flanking the DNA sequence of interest with a protelomerase; and wherein step (c) is performed by:

(c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments.

10. The process according to claim 1, wherein step (a) is performed by contacting a plasmid vector comprising at least two restriction sites flanking the DNA sequence of interest and no protelomerase target sites with at least one restriction enzyme thereby producing open double stranded DNA containing the DNA sequence of interest, and attaching single stranded DNA adaptors to both ends of the open double stranded DNA containing the DNA sequence of interest, with the proviso that the single stranded DNA adaptors do not contain protelomerase target sites; and wherein step (c) is performed by:

(c.1) contacting the concatameric DNA with at least one restriction enzyme thereby producing a plurality of open double stranded DNA fragments each containing the DNA sequence of interest, and (c.2) attaching a single stranded DNA adaptor to each of both ends of the open double stranded DNA fragments.

11. The process according to claim 1, wherein the sequence of interest comprises inverted terminal repeats (ITRs) and an expression cassette, wherein the expression cassette is flanked by the inverted terminal repeats (ITRs).

12. The process according to claim 7, wherein the single stranded DNA adaptor comprises modified oligonucleotides.

13. The process according to claim 1, which is a cell-free in vitro process.

14. A closed linear DNA obtainable according to the process as defined in claim 1.

15. A pharmaceutical composition comprising a therapeutically effective amount of the closed linear DNA according to claim 14 and a pharmaceutically acceptable carrier or an excipient.

* * * * *

SEQUENCE LISTING

```
<160> NUMBER OF SEQ ID NOS: 23

<210> SEQ ID NO 1
<211> LENGTH: 293
<212> TYPE: PRT
<213> ORGANISM: Thermus thermophilus

<400> SEQUENCE: 1

Met Arg Pro Ile Glu His Ala Leu Ser Tyr Ala Ala Gln Gly Tyr Gly
1               5                   10                  15

Val Leu Pro Leu Arg Pro Gly Gly Lys Glu Pro Leu Gly Lys Leu Val
            20                  25                  30

Pro His Gly Leu Lys Asn Ala Ser Arg Asp Pro Ala Thr Leu Glu Ala
        35                  40                  45

Trp Trp Arg Ser Cys Pro Arg Cys Gly Val Gly Ile Leu Pro Gly Pro
    50                  55                  60

Glu Val Leu Val Leu Asp Phe Asp Asp Pro Glu Ala Trp Glu Gly Leu
65                  70                  75                  80

Arg Gln Glu His Pro Ala Leu Glu Ala Ala Pro Arg Gln Arg Thr Pro
                85                  90                  95

Lys Gly Gly Arg His Val Phe Leu Arg Leu Pro Glu Gly Val Arg Leu
            100                 105                 110

Ser Ala Ser Val Arg Ala Ile Pro Gly Val Asp Leu Arg Gly Met Gly
        115                 120                 125

Arg Ala Tyr Val Val Ala Ala Pro Thr Arg Leu Lys Asp Gly Arg Thr
    130                 135                 140
```

```
Tyr Thr Trp Glu Ala Pro Leu Thr Pro Pro Glu Glu Leu Pro Pro Val
145                 150                 155                 160

Pro Gln Ala Leu Leu Leu Lys Leu Leu Pro Pro Pro Pro Pro Pro Arg
                165                 170                 175

Pro Ser Trp Gly Ala Val Gly Thr Ala Ser Pro Lys Arg Leu Gln Ala
            180                 185                 190

Leu Leu Gln Ala Tyr Ala Ala Gln Val Ala Arg Thr Pro Glu Gly Gln
        195                 200                 205

Arg His Leu Thr Leu Ile Arg Tyr Ala Val Ala Ala Gly Gly Leu Ile
    210                 215                 220

Pro His Gly Leu Asp Pro Arg Glu Ala Glu Glu Val Leu Val Ala Ala
225                 230                 235                 240

Ala Met Ser Ala Gly Leu Pro Glu Trp Glu Ala Arg Asp Ala Val Arg
                245                 250                 255

Trp Gly Leu Gly Val Gly Ala Ser Arg Pro Leu Val Leu Glu Ser Ser
            260                 265                 270

Ser Lys Pro Pro Glu Pro Arg Thr Tyr Arg Ala Arg Val Tyr Ala Arg
        275                 280                 285

Met Arg Arg Trp Val
    290


<210> SEQ ID NO 2
<211> LENGTH: 631
<212> TYPE: PRT
<213> ORGANISM: Artificial
<220> FEATURE:
<223> OTHER INFORMATION: TelN

<400> SEQUENCE: 2

Met Ser Lys Val Lys Ile Gly Glu Leu Ile Asn Thr Leu Val Asn Glu
1               5                   10                  15

Val Glu Ala Ile Asp Ala Ser Asp Arg Pro Gln Gly Asp Lys Thr Lys
            20                  25                  30

Arg Ile Lys Ala Ala Ala Ala Arg Tyr Lys Asn Ala Leu Phe Asn Asp
        35                  40                  45

Lys Arg Lys Phe Arg Gly Lys Gly Leu Gln Lys Arg Ile Thr Ala Asn
    50                  55                  60

Thr Phe Asn Ala Tyr Met Ser Arg Ala Arg Lys Arg Phe Asp Asp Lys
65                  70                  75                  80

Leu His His Ser Phe Asp Lys Asn Ile Asn Lys Leu Ser Glu Lys Tyr
                85                  90                  95

Pro Leu Tyr Ser Glu Glu Leu Ser Ser Trp Leu Ser Met Pro Thr Ala
            100                 105                 110

Asn Ile Arg Gln His Met Ser Ser Leu Gln Ser Lys Leu Lys Glu Ile
        115                 120                 125

Met Pro Leu Ala Glu Glu Leu Ser Asn Val Arg Ile Gly Ser Lys Gly
    130                 135                 140

Ser Asp Ala Lys Ile Ala Arg Leu Ile Lys Lys Tyr Pro Asp Trp Ser
145                 150                 155                 160

Phe Ala Leu Ser Asp Leu Asn Ser Asp Asp Trp Lys Glu Arg Arg Asp
                165                 170                 175

Tyr Leu Tyr Lys Leu Phe Gln Gln Gly Ser Ala Leu Leu Glu Glu Leu
            180                 185                 190

His Gln Leu Lys Val Asn His Glu Val Leu Tyr His Leu Gln Leu Ser
        195                 200                 205
```

```
Pro Ala Glu Arg Thr Ser Ile Gln Gln Arg Trp Ala Asp Val Leu Arg
    210                 215                 220

Glu Lys Lys Arg Asn Val Val Val Ile Asp Tyr Pro Thr Tyr Met Gln
225                 230                 235                 240

Ser Ile Tyr Asp Ile Leu Asn Asn Pro Ala Thr Leu Phe Ser Leu Asn
                245                 250                 255

Thr Arg Ser Gly Met Ala Pro Leu Ala Phe Ala Leu Ala Ala Val Ser
            260                 265                 270

Gly Arg Arg Met Ile Glu Ile Met Phe Gln Gly Glu Phe Ala Val Ser
        275                 280                 285

Gly Lys Tyr Thr Val Asn Phe Ser Gly Gln Ala Lys Lys Arg Ser Glu
    290                 295                 300

Asp Lys Ser Val Thr Arg Thr Ile Tyr Thr Leu Cys Glu Ala Lys Leu
305                 310                 315                 320

Phe Val Glu Leu Leu Thr Glu Leu Arg Ser Cys Ser Ala Ala Ser Asp
                325                 330                 335

Phe Asp Glu Val Val Lys Gly Tyr Gly Lys Asp Asp Thr Arg Ser Glu
            340                 345                 350

Asn Gly Arg Ile Asn Ala Ile Leu Ala Lys Ala Phe Asn Pro Trp Val
        355                 360                 365

Lys Ser Phe Phe Gly Asp Asp Arg Arg Val Tyr Lys Asp Ser Arg Ala
    370                 375                 380

Ile Tyr Ala Arg Ile Ala Tyr Glu Met Phe Phe Arg Val Asp Pro Arg
385                 390                 395                 400

Trp Lys Asn Val Asp Glu Asp Val Phe Phe Met Glu Ile Leu Gly His
                405                 410                 415

Asp Asp Glu Asn Thr Gln Leu His Tyr Lys Gln Phe Lys Leu Ala Asn
            420                 425                 430

Phe Ser Arg Thr Trp Arg Pro Glu Val Gly Asp Glu Asn Thr Arg Leu
        435                 440                 445

Val Ala Leu Gln Lys Leu Asp Asp Glu Met Pro Gly Phe Ala Arg Gly
    450                 455                 460

Asp Ala Gly Val Arg Leu His Glu Thr Val Lys Gln Leu Val Glu Gln
465                 470                 475                 480

Asp Pro Ser Ala Lys Ile Thr Asn Ser Thr Leu Arg Ala Phe Lys Phe
                485                 490                 495

Ser Pro Thr Met Ile Ser Arg Tyr Leu Glu Phe Ala Ala Asp Ala Leu
            500                 505                 510

Gly Gln Phe Val Gly Glu Asn Gly Gln Trp Gln Leu Lys Ile Glu Thr
        515                 520                 525

Pro Ala Ile Val Leu Pro Asp Glu Glu Ser Val Glu Thr Ile Asp Glu
    530                 535                 540

Pro Asp Asp Glu Ser Gln Asp Asp Glu Leu Asp Glu Asp Glu Ile Glu
545                 550                 555                 560

Leu Asp Glu Gly Gly Gly Asp Glu Pro Thr Glu Glu Glu Gly Pro Glu
                565                 570                 575

Glu His Gln Pro Thr Ala Leu Lys Pro Val Phe Lys Pro Ala Lys Asn
            580                 585                 590

Asn Gly Asp Gly Thr Tyr Lys Ile Glu Phe Glu Tyr Asp Gly Lys His
        595                 600                 605

Tyr Ala Trp Ser Gly Pro Ala Asp Ser Pro Met Ala Ala Met Arg Ser
    610                 615                 620
```

Ala Trp Glu Thr Tyr Tyr Ser
625 630

<210> SEQ ID NO 3
<211> LENGTH: 56
<212> TYPE: DNA
<213> ORGANISM: Artificial
<220> FEATURE:
<223> OTHER INFORMATION: TelN target sequence

<400> SEQUENCE: 3
tatcagcaca caattgccca ttatacgcgc gtataatgga ctattgtgtg ctgata 56

<210> SEQ ID NO 4
<211> LENGTH: 41
<212> TYPE: DNA
<213> ORGANISM: Artificial
<220> FEATURE:
<223> OTHER INFORMATION: AflII adaptor

<400> SEQUENCE: 4
ttaagtaaca tttgttggcc actcaggcca acaaatgtta c 41

<210> SEQ ID NO 5
<211> LENGTH: 41
<212> TYPE: DNA
<213> ORGANISM: Artificial
<220> FEATURE:
<223> OTHER INFORMATION: NheI-HF adaptor

<400> SEQUENCE: 5
ctagctaaca tttgttggcc actcaggcca acaaatgtta g 41

<210> SEQ ID NO 6
<211> LENGTH: 40
<212> TYPE: DNA
<213> ORGANISM: Artificial
<220> FEATURE:
<223> OTHER INFORMATION: EcoRV adaptor

<400> SEQUENCE: 6
tctaacattt gttggccact caggccaaca aatgttagat 40

<210> SEQ ID NO 7
<211> LENGTH: 40
<212> TYPE: DNA
<213> ORGANISM: Artificial
<220> FEATURE:
<223> OTHER INFORMATION: ScaI adaptor

<400> SEQUENCE: 7
cttaacattt gttggccact caggccaaca aatgttaagt 40

<210> SEQ ID NO 8
<211> LENGTH: 141
<212> TYPE: DNA
<213> ORGANISM: Artificial
<220> FEATURE:
<223> OTHER INFORMATION: 5' ITR sequence

<400> SEQUENCE: 8
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc t 141

<210> SEQ ID NO 9
<211> LENGTH: 141
<212> TYPE: DNA
<213> ORGANISM: Artificial
<220> FEATURE:
<223> OTHER INFORMATION: 3' ITR sequence

<400> SEQUENCE: 9
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctgcctgcag g 141

<210> SEQ ID NO 10
<211> LENGTH: 17
<212> TYPE: DNA
<213> ORGANISM: Artificial Sequence
<220> FEATURE:
<223> OTHER INFORMATION: oligo 15

<400> SEQUENCE: 10
agggatccac tcaggat 17

<210> SEQ ID NO 11
<211> LENGTH: 17
<212> TYPE: DNA
<213> ORGANISM: Artificial Sequence
<220> FEATURE:
<223> OTHER INFORMATION: oligo 37
<220> FEATURE:
<221> NAME/KEY: modified_base
<222> LOCATION: (9)..(13)
<223> OTHER INFORMATION: phosphothioated nucleotides

<400> SEQUENCE: 11
agggatccac tcaggat 17

<210> SEQ ID NO 12
<211> LENGTH: 21
<212> TYPE: DNA
<213> ORGANISM: Artificial Sequence
<220> FEATURE:
<223> OTHER INFORMATION: oligo 4

<400> SEQUENCE: 12
agggctaacc actcaggtta g 21

<210> SEQ ID NO 13
<211> LENGTH: 21
<212> TYPE: DNA
<213> ORGANISM: Artificial Sequence
<220> FEATURE:
<223> OTHER INFORMATION: oligo 28
<220> FEATURE:
<221> NAME/KEY: modified_base
<222> LOCATION: (11)..(11)
<223> OTHER INFORMATION: 8-oxo-deoxyadenosine
<220> FEATURE:
<221> NAME/KEY: modified_base
<222> LOCATION: (15)..(15)
<223> OTHER INFORMATION: 8-oxo-deoxyadenosine

<400> SEQUENCE: 13
agggctaacc actcaggtta g 21

<210> SEQ ID NO 14
<211> LENGTH: 21

<212> TYPE: DNA
<213> ORGANISM: Artificial Sequence
<220> FEATURE:
<223> OTHER INFORMATION: oligo 29
<220> FEATURE:
<221> NAME/KEY: modified_base
<222> LOCATION: (12)..(12)
<223> OTHER INFORMATION: 5-Fluoro-deoxyuracil
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (14)..(14)
<223> OTHER INFORMATION: 5-Fluoro-deoxyuracil
<220> FEATURE:
<221> NAME/KEY: misc_feature
<222> LOCATION: (14)..(14)
<223> OTHER INFORMATION: n is a, c, g, or t

<400> SEQUENCE: 14
agggctaacc antnaggtta g 21

<210> SEQ ID NO 15
<211> LENGTH: 31
<212> TYPE: DNA
<213> ORGANISM: Artificial Sequence
<220> FEATURE:
<223> OTHER INFORMATION: oligo 17

<400> SEQUENCE: 15
agggataaca tggccactca ggccatgtta t 31

<210> SEQ ID NO 16
<211> LENGTH: 25
<212> TYPE: DNA
<213> ORGANISM: Artificial Sequence
<220> FEATURE:
<223> OTHER INFORMATION: oligo 19
<220> FEATURE:
<221> NAME/KEY: modified_base
<222> LOCATION: (11)..(15)
<223> OTHER INFORMATION: LNA nucleotides

<400> SEQUENCE: 16
agggataaca tggccactca ggcca 25

<210> SEQ ID NO 17
<211> LENGTH: 31
<212> TYPE: DNA
<213> ORGANISM: Artificial Sequence
<220> FEATURE:
<223> OTHER INFORMATION: oligo 22
<220> FEATURE:
<221> NAME/KEY: modified_base
<222> LOCATION: (16)..(16)
<223> OTHER INFORMATION: 8-oxo-deoxyadenosine
<220> FEATURE:
<221> NAME/KEY: modified_base
<222> LOCATION: (20)..(20)
<223> OTHER INFORMATION: 8-oxo-deoxyadenosine

<400> SEQUENCE: 17
agggataaca tggccactca ggccatgtta t 31

<210> SEQ ID NO 18
<211> LENGTH: 31
<212> TYPE: DNA
<213> ORGANISM: Artificial Sequence
<220> FEATURE:

<223> OTHER INFORMATION: oligo 21
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: modified_base
<222> LOCATION: (20)..(20)
<223> OTHER INFORMATION: I
<220> FEATURE:
<221> NAME/KEY: misc_feature
<222> LOCATION: (20)..(20)
<223> OTHER INFORMATION: n is a, c, g, or t

<400> SEQUENCE: 18
agggataaca tggccnctcn ggccatgtta t 31

<210> SEQ ID NO 19
<211> LENGTH: 18
<212> TYPE: DNA
<213> ORGANISM: Artificial Sequence
<220> FEATURE:
<223> OTHER INFORMATION: oligo 41
<220> FEATURE:
<221> NAME/KEY: modified_base
<222> LOCATION: (11)..(14)
<223> OTHER INFORMATION: phosphothioated nucleotide

<400> SEQUENCE: 19
agggcttacg cgcgtaag 18

<210> SEQ ID NO 20
<211> LENGTH: 3762
<212> TYPE: DNA
<213> ORGANISM: Artificial Sequence
<220> FEATURE:
<223> OTHER INFORMATION: eGFP plasmid

<400> SEQUENCE: 20
ccaatgatgg taccgtatca gcacacaatt gcccattata cgcgcgtata atggactatt 60
gtgtgctgat aggtctcgcc ctgatttaaa tcgtcgaccg ttacataact tacggtaaat 120
ggcccgcctg gctgaccgcc caacgacccc cgcccattga cgtcaataat gacgtatgtt 180
cccatagtaa cgccaatagg gactttccat tgacgtcaat gggtggagta tttacggtaa 240
actgcccact tggcagtaca tcaagtgtat catatgccaa gtacgccccc tattgacgtc 300
aatgacggta aatggcccgc ctggcattat gcccagtaca tgaccttatg ggactttcct 360
acttggcagt acatctacgt attagtcatc gctattacca tggtgatgcg gttttggcag 420
tacatcaatg ggcgtggata gcggtttgac tcacggggat ttccaagtct ccaccccatt 480
gacgtcaatg ggagtttgtt ttggcaccaa aatcaacggg actttccaaa atgtcgtaac 540
aactccgccc cattgacgca aatgggcggt aggcgtgtac ggtgggaggt ctatataagc 600
agagctcgtt tagtgaaccg tcagatcgcc tggagacgcc atccacgctg ttttgacctc 660
catagaagac accgggaccg atccagcctc cggactctag aggatccggt actcgaggaa 720
ctgaaaaacc agaaagttaa ctggtaagtt tagtcttttt gtcttttatt tcaggtcccg 780
gatccggtgg tggtgcaaat caaagaactg ctcctcagtg gatgttgcct ttacttctag 840
gcctgtacgg aagtgttact tctgctctaa aagctgcgga attgtacccg cggcccggga 900
tccaccggtc gccaccatgg tgagcaaggg cgaggagctg ttcaccgggg tggtgcccat 960

-continued

```
cctggtcgag ctggacggcg acgtaaacgg ccacaagttc agcgtgtccg gcgagggcga   1020
gggcgatgcc acctacggca agctgaccct gaagttcatc tgcaccaccg gcaagctgcc   1080
cgtgccctgg cccaccctcg tgaccaccct gacctacggc gtgcagtgct tcagccgcta   1140
ccccgaccac atgaagcagc acgacttctt caagtccgcc atgcccgaag gctacgtcca   1200
ggagcgcacc atcttcttca aggacgacgg caactacaag acccgcgccg aggtgaagtt   1260
cgagggcgac accctggtga accgcatcga gctgaagggc atcgacttca aggaggacgg   1320
caacatcctg gggcacaagc tggagtacaa ctacaacagc cacaacgtct atatcatggc   1380
cgacaagcag aagaacggca tcaaggtgaa cttcaagatc cgccacaaca tcgaggacgg   1440
cagcgtgcag ctcgccgacc actaccagca gaacaccccc atcggcgacg gccccgtgct   1500
gctgcccgac aaccactacc tgagcaccca gtccgccctg agcaaagacc ccaacgagaa   1560
gcgcgatcac atggtcctgc tggagttcgt gaccgccgcc gggatcactc tcggcatgga   1620
cgagctgtac aagtaaagcg gccgcgggga tccagacatg ataagataca ttgatgagtt   1680
tggacaaacc acaactagaa tgcagtgaaa aaaatgcttt atttgtgaaa tttgtgatgc   1740
tattgcttta tttgtaacca ttataagctg caataaacaa gttaacaaca acaattgcat   1800
tcattttatg tttcaggttc agggggaggt gtgggaggtt ttttagtcga ccatttaaat   1860
cggtctcgag ggtatcagca cacaattgcc cattatacgc gcgtataatg gactattgtg   1920
tgctgataga agcttatcgg aaagaacatg tgagcaaaag gccagcaaaa ggccaggaac   1980
cgtaaaaagg ccgcgttgct ggcgtttttc cataggctcc gcccccctga cgagcatcac   2040
aaaaatcgac gctcaagtca gaggtggcga aacccgacag gactataaag ataccaggcg   2100
tttccccctg gaagctccct cgtgcgctct cctgttccga ccctgccgct taccggatac   2160
ctgtccgcct ttctcccttc gggaagcgtg gcgctttctc atagctcacg ctgtaggtat   2220
ctcagttcgg tgtaggtcgt tcgctccaag ctgggctgtg tgcacgaacc ccccgttcag   2280
cccgaccgct gcgccttatc cggtaactat cgtcttgagt ccaacccggt aagacacgac   2340
ttatcgccac tggcagcagc cactggtaac aggattagca gagcgaggta tgtaggcggt   2400
gctacagagt tcttgaagtg gtggcctaac tacggctaca ctagaagaac agtatttggt   2460
atctgcgctc tgctgaagcc agttaccttc ggaaaaagag ttggtagctc ttgatccggc   2520
aaacaaacca ccgctggtag cggtggtttt tttgtttgca agcagcagat tacgcgcaga   2580
aaaaaaggat ctcaagaaga tcctttgatc ttttctacgg ggtctgacgc tcagtggaac   2640
gaaaactcac gttaagggat tttggtcatg agattatcaa aaaggatctt cacctagatc   2700
cttttaaatt aaaaatgaag ttttaaatca atctaaagta tatatgagta aacttggtct   2760
gacagttacc aatgcttaat cagtgaggca cctatctcag cgatctgtct atttcgttca   2820
tccatagttg cctgactccc cgtcgtgtag ataactacga tacgggaggg cttaccatct   2880
ggccccagtg ctgcaatgat accgcgagac ccacgctcac cggctccaga tttatcagca   2940
ataaaccagc cagccggaag ggccgagcgc agaagtggtc ctgcaacttt atccgcctcc   3000
atccagtcta ttaattgttg ccgggaagct agagtaagta gttcgccagt taatagtttg   3060
cgcaacgttg ttgccattgc tacaggcatc gtggtgtcac gctcgtcgtt tggtatggct   3120
tcattcagct ccggttccca acgatcaagg cgagttacat gatcccccat gttgtgcaaa   3180
aaagcggtta gctccttcgg tcctccgatc gttgtcagaa gtaagttggc cgcagtgtta   3240
tcactcatgg ttatggcagc actgcataat tctcttactg tcatgccatc cgtaagatgc   3300
```

ttttctgtga ctggtgagta ctcaaccaag tcattctgag aatagtgtat gcggcgaccg 3360
agttgctctt gcccggcgtc aatacgggat aataccgcgc cacatagcag aactttaaaa 3420
gtgctcatca ttggaaaacg ttcttcgggg cgaaaactct caaggatctt accgctgttg 3480
agatccagtt cgatgtaacc cactcgtgca cccaactgat cttcagcatc ttttactttc 3540
accagcgttt ctgggtgagc aaaaacagga aggcaaaatg ccgcaaaaaa gggaataagg 3600
gcgacacgga aatgttgaat actcatactc ttcctttttc aatattattg aagcatttat 3660
cagggttatt gtctcatgag cggatacata tttgaatgta tttagaaaaa taaacaaata 3720
ggggttccgc gcacatttcc ccgaaaagtg ccacctgacg tc 3762

<210> SEQ ID NO 21
<211> LENGTH: 4695
<212> TYPE: DNA
<213> ORGANISM: Artificial Sequence
<220> FEATURE:
<223> OTHER INFORMATION: Luc plasmid

<400> SEQUENCE: 21
ccaatgatgg taccgtatca gcacacaatt gcccattata cgcgcgtata atggactatt 60
gtgtgctgat aggtctcgcc ctgatttaaa tcgtcgaccg ttacataact tacggtaaat 120
ggcccgcctg gctgaccgcc caacgacccc cgcccattga cgtcaataat gacgtatgtt 180
cccatagtaa cgccaatagg gactttccat tgacgtcaat gggtggagta tttacggtaa 240
actgcccact tggcagtaca tcaagtgtat catatgccaa gtacgccccc tattgacgtc 300
aatgacggta aatggcccgc ctggcattat gcccagtaca tgaccttatg ggactttcct 360
acttggcagt acatctacgt attagtcatc gctattacca tggtgatgcg gttttggcag 420
tacatcaatg ggcgtggata gcggtttgac tcacggggat ttccaagtct ccacccccatt 480 gacgtcaatg ggagtttgtt ttggcaccaa aatcaacggg actttccaaa atgtcgtaac 540
aactccgccc cattgacgca aatgggcggt aggcgtgtac ggtgggaggt ctatataagc 600
agagctcgtt tagtgaaccg tcagatcgcc tggagacgcc atccacgctg ttttgacctc 660
catagaagac accgggaccg atccagcctc cggactctag aggatccggt actcgaggaa 720
ctgaaaaacc agaaagttaa ctggtaagtt tagtcttttt gtcttttatt tcaggtcccg 780
gatccggtgg tggtgcaaat caaagaactg ctcctcagtg gatgttgcct ttacttctag 840
gcctgtacgg aagtgttact tctgctctaa aagctgcgga attgtacccg cggcccggga 900
tccaccggtc gccaccatgg aagacgccaa aaacataaag aaaggcccgg cgccattcta 960
tcctctagag gatggaaccg ctggagagca actgcataag gctatgaaga gatacgccct 1020
ggttcctgga acaattgctt ttacagatgc acatatcgag gtgaacatca cgtacgcgga 1080
atacttcgaa atgtccgttc ggttggcaga agctatgaaa cgatatgggc tgaatacaaa 1140
tcacagaatc gtcgtatgca gtgaaaactc tcttcaattc tttatgccgg tgttgggcgc 1200
gttatttatc ggagttgcag ttgcgcccgc gaacgacatt tataatgaac gtgaattgct 1260
caacagtatg aacatttcgc agcctaccgt agtgtttgtt tccaaaaagg ggttgcaaaa 1320
aattttgaac gtgcaaaaaa aattaccaat aatccagaaa attattatca tggattctaa 1380
aacggattac cagggatttc agtcgatgta cacgttcgtc acatctcatc tacctcccgg 1440
ttttaatgaa tacgattttg taccagagtc ctttgatcgt gacaaaacaa ttgcactgat 1500
aatgaattcc tctggatcta ctgggttacc taagggtgtg gcccttccgc atagaactgc 1560
ctgcgtcaga ttctcgcatg ccagagatcc tatttttggc aatcaaatca ttccggatac 1620

```
tgcgatttta agtgttgttc cattccatca cggttttgga atgtttacta cactcggata   1680
tttgatatgt ggatttcgag tcgtcttaat gtatagattt gaagaagagc tgtttttacg   1740
atcccttcag gattacaaaa ttcaaagtgc gttgctagta ccaaccctat tttcattctt   1800
cgccaaaagc actctgattg acaaatacga tttatctaat ttacacgaaa ttgcttctgg   1860
gggcgcacct ctttcgaaag aagtcgggga agcggttgca aaacgcttcc atcttccagg   1920
gatacgacaa ggatatgggc tcactgagac tacatcagct attctgatta cacccgaggg   1980
ggatgataaa ccgggcgcgg tcggtaaagt tgttccattt tttgaagcga aggttgtgga   2040
tctggatacc gggaaaacgc tgggcgttaa tcagagaggc gaattatgtg tcagaggacc   2100
tatgattatg tccggttatg taaacaatcc ggaagcgacc aacgccttga ttgacaagga   2160
tggatggcta cattctggag acatagctta ctgggacgaa gacgaacact tcttcatagt   2220
tgaccgcttg aagtctttaa ttaaatacaa aggatatcag gtggcccccg ctgaattgga   2280
atcgatattg ttacaacacc ccaacatctt cgacgcgggc gtggcaggtc ttcccgacga   2340
tgacgccggt gaacttcccg ccgccgttgt tgttttggag cacggaaaga cgatgacgga   2400
aaaagagatc gtggattacg tcgccagtca agtaacaacc gcgaaaaagt tgcgcggagg   2460
agttgtgttt gtggacgaag taccgaaagg tcttaccgga aaactcgacg caagaaaaat   2520
cagagagatc ctcataaagg ccaagaaggg cggaaagtcc aaattgtaaa gcggccgcgg   2580
ggatccagac atgataagat acattgatga gtttggacaa accacaacta gaatgcagtg   2640
aaaaaaatgc tttatttgtg aaatttgtga tgctattgct ttatttgtaa ccattataag   2700
ctgcaataaa caagttaaca acaacaattg cattcatttt atgtttcagg ttcaggggga   2760
ggtgtgggag gtttttagt cgaccattta aatcggtctc gagggtatca gcacacaatt   2820
gcccattata cgcgcgtata atggactatt gtgtgctgat agaagcttat cggaaagaac   2880
atgtgagcaa aaggccagca aaaggccagg aaccgtaaaa aggccgcgtt gctggcgttt   2940
ttccataggc tccgcccccc tgacgagcat cacaaaaatc gacgctcaag tcagaggtgg   3000
cgaaacccga caggactata aagataccag gcgtttcccc ctggaagctc cctcgtgcgc   3060
tctcctgttc cgaccctgcc gcttaccgga tacctgtccg cctttctccc ttcgggaagc   3120
gtggcgcttt ctcatagctc acgctgtagg tatctcagtt cggtgtaggt cgttcgctcc   3180
aagctgggct gtgtgcacga acccccgtt cagcccgacc gctgcgcctt atccggtaac   3240
tatcgtcttg agtccaaccc ggtaagacac gacttatcgc cactggcagc agccactggt   3300
aacaggatta gcagagcgag gtatgtaggc ggtgctacag agttcttgaa gtggtggcct   3360
aactacggct acactagaag aacagtattt ggtatctgcg ctctgctgaa gccagttacc   3420
ttcggaaaaa gagttggtag ctcttgatcc ggcaaacaaa ccaccgctgg tagcggtggt   3480
tttttgttt gcaagcagca gattacgcgc agaaaaaaag gatctcaaga agatcctttg   3540
atcttttcta cggggtctga cgctcagtgg aacgaaaact cacgttaagg gattttggtc   3600
atgagattat caaaaaggat cttcacctag atccttttaa attaaaaatg aagttttaaa   3660
tcaatctaaa gtatatatga gtaaacttgg tctgacagtt accaatgctt aatcagtgag   3720
gcacctatct cagcgatctg tctatttcgt tcatccatag ttgcctgact ccccgtcgtg   3780
tagataacta cgatacggga gggcttacca tctggcccca gtgctgcaat gataccgcga   3840
gacccacgct caccggctcc agatttatca gcaataaacc agccagccgg aagggccgag   3900
cgcagaagtg gtcctgcaac tttatccgcc tccatccagt ctattaattg ttgccgggaa   3960
```

gctagagtaa gtagttcgcc agttaatagt ttgcgcaacg ttgttgccat tgctacaggc 4020
atcgtggtgt cacgctcgtc gtttggtatg gcttcattca gctccggttc ccaacgatca 4080
aggcgagtta catgatcccc catgttgtgc aaaaaagcgg ttagctcctt cggtcctccg 4140
atcgttgtca gaagtaagtt ggccgcagtg ttatcactca tggttatggc agcactgcat 4200
aattctctta ctgtcatgcc atccgtaaga tgcttttctg tgactggtga gtactcaacc 4260
aagtcattct gagaatagtg tatgcggcga ccgagttgct cttgcccggc gtcaatacgg 4320
gataataccg cgccacatag cagaacttta aaagtgctca tcattggaaa acgttcttcg 4380
gggcgaaaac tctcaaggat cttaccgctg ttgagatcca gttcgatgta acccactcgt 4440
gcacccaact gatcttcagc atcttttact ttcaccagcg tttctgggtg agcaaaaaca 4500
ggaaggcaaa atgccgcaaa aaagggaata agggcgacac ggaaatgttg aatactcata 4560
ctcttccttt ttcaatatta ttgaagcatt tatcagggtt attgtctcat gagcggatac 4620
atatttgaat gtatttagaa aaataaacaa ataggggttc cgcgcacatt tccccgaaaa 4680
gtgccacctg acgtc 4695

<210> SEQ ID NO 22
<211> LENGTH: 4902
<212> TYPE: DNA
<213> ORGANISM: Artificial Sequence
<220> FEATURE:
<223> OTHER INFORMATION: Luc-ITR plasmid

<400> SEQUENCE: 22
ccaatgatgg taccgtatca gcacacaatt gcccattata cgcgcgtata atggactatt 60
gtgtgctgat agataggtct cgccctcctg caggcagctg cgcgctcgct cgctcactga 120
ggccgcccgg gcaaagcccg ggcgtcgggc gacctttggt cgcccggcct cagtgagcga 180
gcgagcgcgc agagagggag tggccaactc catcactagg ggttcctgcg gccgcacgcg 240
tcgttacata acttacggta aatggcccgc ctggctgacc gcccaacgac ccccgcccat 300
tgacgtcaat agtaacgcca atagggactt tccattgacg tcaatgggtg gagtatttac 360
ggtaaactgc ccacttggca gtacatcaag tgtatcatat gccaagtacg ccccctattg 420
acgtcaatga cggtaaatgg cccgcctggc attgtgccca gtacatgacc ttatgggact 480
ttcctacttg gcagtacatc tacgtattag tcatcgctat taccatggtg atgcggtttt 540
ggcagtacat caatgggcgt ggatagcggt ttgactcacg gggatttcca agtctccacc 600
ccattgacgt caatgggagt ttgttttggc accaaaatca acgggacttt ccaaaatgtc 660
gtaacaactc cgccccattg acgcaaatgg gcggtaggcg tgtacggtgg gaggtctata 720
taagcagagc tgctagcttg gcattccggt actgttggta aagccaccat ggaagacgcc 780
aaaaacataa agaaaggccc ggcgccattc tatccgctgg aagatggaac cgctggagag 840
caactgcata aggctatgaa gagatacgcc ctggttcctg gaacaattgc ttttacagat 900
gcacatatcg aggtggacat cacttacgct gagtacttcg aaatgtccgt tcggttggca 960
gaagctatga aacgatatgg gctgaataca aatcacagaa tcgtcgtatg cagtgaaaac 1020
tctcttcaat tctttatgcc ggtgttgggc gcgttattta tcggagttgc agttgcgccc 1080
gcgaacgaca tttataatga acgtgaattg ctcaacagta tgggcatttc gcagcctacc 1140
gtggtgttcg tttccaaaaa ggggttgcaa aaaattttga acgtgcaaaa aaagctccca 1200
atcatccaaa aaattattat catggattct aaaacggatt accagggatt tcagtcgatg 1260
tacacgttcg tcacatctca tctacctccc ggttttaatg aatacgattt tgtgccagag 1320

```
tccttcgata gggacaagac aattgcactg atcatgaact cctctggatc tactggtctg   1380
cctaaaggtg tcgctctgcc tcatagaact gcctgcgtga gattctcgca tgccagagat   1440
cctatttttg gcaatcaaat cattccggat actgcgattt taagtgttgt tccattccat   1500
cacggttttg gaatgtttac tacactcgga tatttgatat gtggatttcg agtcgtctta   1560
atgtatagat ttgaagaaga gctgtttctg aggagccttc aggattacaa gattcaaagt   1620
gcgctgctgg tgccaaccct attctccttc ttcgccaaaa gcactctgat tgacaaatac   1680
gatttatcta atttacacga aattgcttct ggtggcgctc ccctctctaa ggaagtcggg   1740
gaagcggttg ccaagaggtt ccatctgcca ggtatcaggc aaggatatgg gctcactgag   1800
actacatcag ctattctgat tacacccgag ggggatgata aaccgggcgc ggtcggtaaa   1860
gttgttccat tttttgaagc gaaggttgtg gatctggata ccgggaaaac gctgggcgtt   1920
aatcaaagag gcgaactgtg tgtgagaggt cctatgatta tgtccggtta tgtaaacaat   1980
ccggaagcga ccaacgcctt gattgacaag gatggatggc tacattctgg agacatagct   2040
tactgggacg aagacgaaca cttcttcatc gttgaccgcc tgaagtctct gattaagtac   2100
aaaggctatc aggtggctcc cgctgaattg gaatccatct tgctccaaca ccccaacatc   2160
ttcgacgcag gtgtcgcagg tcttcccgac gatgacgccg gtgaacttcc cgccgccgtt   2220
gttgttttgg agcacggaaa gacgatgacg gaaaaagaga tcgtggatta cgtcgccagt   2280
caagtaacaa ccgcgaaaaa gttgcgcgga ggagttgtgt ttgtggacga agtaccgaaa   2340
ggtcttaccg gaaaactcga cgcaagaaaa atcagagaga tcctcataaa ggccaagaag   2400
ggcggaaaga tcgccgtgtc aagccatggc ttcccgccgg cggtggcggc gcaggatgat   2460
ggcacgctgc ccatgtcttg tgcccaggag agcgggatgg accgtcaccc tgcagcctgt   2520
gcttctgcta ggatcaatgt gtaggcggcc aacaatgcga tccgatggcc gcgactctag   2580
agtcggggcg gccggccgct tcgagcagac atgataagat acattgatga gtttggacaa   2640
accacaacta gaatgcagtg aaaaaaatgc tttatttgtg aaatttgtga tgctattgct   2700
ttatttgtaa ccattataag ctgcaataaa caagttaaca acaacaattg cattcatttt   2760
atgtttcagg ttcaggggga ggtgtgggag gtttttaaa gcaagtaaaa cctctacaaa   2820
tgtggtaaaa tcgataagcc cgtgcggacc gagcggccgc aggaacccct agtgatggag   2880
ttggccactc cctctctgcg cgctcgctcg ctcactgagg ccgggcgacc aaaggtcgcc   2940
cgacgcccgg gctttgcccg ggcggcctca gtgagcgagc gagcgcgcag ctgcctgcag   3000
gggtctcgag ggtatcagca cacaattgcc cattatacgc gcgtataatg gactattgtg   3060
tgctgataga agcttatcgg aaagaacatg tgagcaaaag gccagcaaaa ggccaggaac   3120
cgtaaaaagg ccgcgttgct ggcgtttttc cataggctcc gcccccctga cgagcatcac   3180
aaaaatcgac gctcaagtca gaggtggcga aacccgacag gactataaag ataccaggcg   3240
tttccccctg gaagctccct cgtgcgctct cctgttccga ccctgccgct taccggatac   3300
ctgtccgcct ttctcccttc gggaagcgtg gcgctttctc atagctcacg ctgtaggtat   3360
ctcagttcgg tgtaggtcgt tcgctccaag ctgggctgtg tgcacgaacc ccccgttcag   3420
cccgaccgct gcgccttatc cggtaactat cgtcttgagt ccaacccggt aagacacgac   3480
ttatcgccac tggcagcagc cactggtaac aggattagca gagcgaggta tgtaggcggt   3540
gctacagagt tcttgaagtg gtggcctaac tacggctaca ctagaagaac agtatttggt   3600
atctgcgctc tgctgaagcc agttaccttc ggaaaaagag ttggtagctc ttgatccggc   3660
```

```
aaacaaacca ccgctggtag cggtggtttt tttgtttgca agcagcagat tacgcgcaga   3720

aaaaaaggat ctcaagaaga tcctttgatc ttttctacgg ggtctgacgc tcagtggaac   3780

gaaaactcac gttaagggat tttggtcatg agattatcaa aaaggatctt cacctagatc   3840

cttttaaatt aaaaatgaag ttttaaatca atctaaagta tatatgagta aacttggtct   3900

gacagttacc aatgcttaat cagtgaggca cctatctcag cgatctgtct atttcgttca   3960

tccatagttg cctgactccc cgtcgtgtag ataactacga tacgggaggg cttaccatct   4020

ggccccagtg ctgcaatgat accgcgagac ccacgctcac cggctccaga tttatcagca   4080

ataaaccagc cagccggaag ggccgagcgc agaagtggtc ctgcaacttt atccgcctcc   4140

atccagtcta ttaattgttg ccgggaagct agagtaagta gttcgccagt taatagtttg   4200

cgcaacgttg ttgccattgc tacaggcatc gtggtgtcac gctcgtcgtt tggtatggct   4260

tcattcagct ccggttccca acgatcaagg cgagttacat gatcccccat gttgtgcaaa   4320

aaagcggtta gctccttcgg tcctccgatc gttgtcagaa gtaagttggc cgcagtgtta   4380

tcactcatgg ttatggcagc actgcataat tctcttactg tcatgccatc cgtaagatgc   4440

ttttctgtga ctggtgagta ctcaaccaag tcattctgag aatagtgtat gcggcgaccg   4500

agttgctctt gcccggcgtc aatacgggat aataccgcgc cacatagcag aactttaaaa   4560

gtgctcatca ttggaaaacg ttcttcgggg cgaaaactct caaggatctt accgctgttg   4620

agatccagtt cgatgtaacc cactcgtgca cccaactgat cttcagcatc ttttactttc   4680

accagcgttt ctgggtgagc aaaaacagga aggcaaaatg ccgcaaaaaa gggaataagg   4740

gcgacacgga aatgttgaat actcatactc ttcctttttc aatattattg aagcatttat   4800

cagggttatt gtctcatgag cggatacata tttgaatgta tttagaaaaa taaacaaata   4860

ggggttccgc gcacatttcc ccgaaaagtg ccacctgacg tc                      4902
```

<210> SEQ ID NO 23
<211> LENGTH: 4403
<212> TYPE: DNA
<213> ORGANISM: Artificial Sequence
<220> FEATURE:
<223> OTHER INFORMATION: pUC57-Kan_TELO-CMV-EGFP

<400> SEQUENCE: 23

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagagaatt cgtatcagca cacaattgcc    420

cattatacgc gcgtataatg gactattgtg tgctgataga tttaaatcgt cgaccgttac    480

ataacttacg gtaaatggcc cgcctggctg accgcccaac gacccccgcc cattgacgtc    540

aataatgacg tatgttccca tagtaacgcc aatagggact ttccattgac gtcaatgggt    600

ggagtattta cggtaaactg cccacttggc agtacatcaa gtgtatcata tgccaagtac    660

gccccctatt gacgtcaatg acggtaaatg gcccgcctgg cattatgccc agtacatgac    720

cttatgggac tttcctactt ggcagtacat ctacgtatta gtcatcgcta ttaccatggt    780

gatgcggttt tggcagtaca tcaatgggcg tggatagcgg tttgactcac ggggatttcc    840
```

```
aagtctccac cccattgacg tcaatgggag tttgttttgg caccaaaatc aacgggactt    900
tccaaaatgt cgtaacaact ccgccccatt gacgcaaatg ggcggtaggc gtgtacggtg    960
ggaggtctat ataagcagag ctcgtttagt gaaccgtcag atcgcctgga gacgccatcc   1020
acgctgtttt gacctccata gaagacaccg ggaccgatcc agcctccgga ctctagagga   1080
tccggtactc gaggaactga aaaaccagaa agttaactgg taagtttagt ctttttgtct   1140
tttatttcag gtcccggatc cggtggtggt gcaaatcaaa gaactgctcc tcagtggatg   1200
ttgcctttac ttctaggcct gtacggaagt gttacttctg ctctaaaagc tgcggaattg   1260
tacccgcggc ccgggatcca ccggtcgcca ccatggtgag caagggcgag gagctgttca   1320
ccggggtggt gcccatcctg gtcgagctgg acggcgacgt aaacggccac aagttcagcg   1380
tgtccggcga gggcgagggc gatgccacct acggcaagct gaccctgaag ttcatctgca   1440
ccaccggcaa gctgcccgtg ccctggccca ccctcgtgac caccctgacc tacggcgtgc   1500
agtgcttcag ccgctacccc gaccacatga agcagcacga cttcttcaag tccgccatgc   1560
ccgaaggcta cgtccaggag cgcaccatct tcttcaagga cgacggcaac tacaagaccc   1620
gcgccgaggt gaagttcgag ggcgacaccc tggtgaaccg catcgagctg aagggcatcg   1680
acttcaagga ggacggcaac atcctggggc acaagctgga gtacaactac aacagccaca   1740
acgtctatat catggccgac aagcagaaga acggcatcaa ggtgaacttc aagatccgcc   1800
acaacatcga ggacggcagc gtgcagctcg ccgaccacta ccagcagaac acccccatcg   1860
gcgacggccc cgtgctgctg cccgacaacc actacctgag cacccagtcc gccctgagca   1920
aagaccccaa cgagaagcgc gatcacatgg tcctgctgga gttcgtgacc gccgccggga   1980
tcactctcgg catggacgag ctgtacaagt aaagcggccg cggggatcca gacatgataa   2040
gatacattga tgagtttgga caaaccacaa ctagaatgca gtgaaaaaaa tgctttattt   2100
gtgaaatttg tgatgctatt gctttatttg taaccattat aagctgcaat aaacaagtta   2160
acaacaacaa ttgcattcat tttatgtttc aggttcaggg ggaggtgtgg gaggtttttt   2220
agtcgaccat ttaaatctat cagcacacaa ttgcccatta tacgcgcgta taatggacta   2280
ttgtgtgctg atagaagctt ggtgtaatca tggtcatagc tgtttcctgt gtgaaattgt   2340
tatccgctca caattccaca caacatacga gccggaagca taaagtgtaa agcctggggt   2400
gcctaatgag tgagctaact cacattaatt gcgttgcgct cactgcccgc tttccagtcg   2460
ggaaacctgt cgtgccagct gcattaatga atcggccaac gcgcggggag aggcggtttg   2520
cgtattgggc gctcttccgc ttcctcgctc actgactcgc tgcgctcggt cgttcggctg   2580
cggcgagcgg tatcagctca ctcaaaggcg gtaatacggt tatccacaga atcaggggat   2640
aacgcaggaa agaacatgtg agcaaaaggc cagcaaaagg ccaggaaccg taaaaaggcc   2700
gcgttgctgg cgtttttcca taggctccgc ccccctgacg agcatcacaa aaatcgacgc   2760
tcaagtcaga ggtggcgaaa cccgacagga ctataaagat accaggcgtt tccccctgga   2820
agctccctcg tgcgctctcc tgttccgacc ctgccgctta ccggatacct gtccgccttt   2880
ctcccttcgg gaagcgtggc gctttctcat agctcacgct gtaggtatct cagttcggtg   2940
taggtcgttc gctccaagct gggctgtgtg cacgaacccc ccgttcagcc cgaccgctgc   3000
gccttatccg gtaactatcg tcttgagtcc aacccggtaa gacacgactt atcgccactg   3060
gcagcagcca ctggtaacag gattagcaga gcgaggtatg taggcggtgc tacagagttc   3120
ttgaagtggt ggcctaacta cggctacact agaagaacag tatttggtat ctgcgctctg   3180
```

-continued

```
ctgaagccag ttaccttcgg aaaaagagtt ggtagctctt gatccggcaa acaaaccacc   3240

gctggtagcg gtggtttttt tgtttgcaag cagcagatta cgcgcagaaa aaaggatct    3300

caagaagatc ctttgatctt ttctacgggg tctgacgctc agtggaacga aaactcacgt   3360

taagggattt tggtcatgag attatcaaaa aggatcttca cctagatcct tttaaattaa   3420

aaatgaagtt ttaaatcaag cccaatctga ataatgttac aaccaattaa ccaattctga   3480

ttagaaaaac tcatcgagca tcaaatgaaa ctgcaattta ttcatatcag gattatcaat   3540

accatatttt tgaaaaagcc gtttctgtaa tgaaggagaa aactcaccga ggcagttcca   3600

taggatggca agatcctggt atcggtctgc gattccgact cgtccaacat caatacaacc   3660

tattaatttc ccctcgtcaa aaataaggtt atcaagtgag aaatcaccat gagtgacgac   3720

tgaatccggt gagaatggca aaagtttatg catttctttc cagacttgtt caacaggcca   3780

gccattacgc tcgtcatcaa aatcactcgc atcaaccaaa ccgttattca ttcgtgattg   3840

cgcctgagcg agacgaaata cgcgatcgct gttaaaagga caattacaaa caggaatcga   3900

atgcaaccgg cgcaggaaca ctgccagcgc atcaacaata ttttcacctg aatcaggata   3960

ttcttctaat acctggaatg ctgtttttcc ggggatcgca gtggtgagta accatgcatc   4020

atcaggagta cggataaaat gcttgatggt cggaagaggc ataaattccg tcagccagtt   4080

tagtctgacc atctcatctg taacatcatt ggcaacgcta cctttgccat gtttcagaaa   4140

caactctggc gcatcgggct tcccatacaa gcgatagatt gtcgcacctg attgcccgac   4200

attatcgcga gcccatttat acccatataa atcagcatcc atgttggaat ttaatcgcgg   4260

cctcgacgtt tcccgttgaa tatggctcat aacacccctt gtattactgt ttatgtaagc   4320

agacagtttt attgttcatg atgatatatt tttatcttgt gcaatgtaac atcagagatt   4380

ttgagacacg ggccagagct gca                                             4403
```